United States Patent

Leppard et al.

[11] Patent Number: 5,300,414
[45] Date of Patent: Apr. 5, 1994

[54] PHOTOGRAPHIC MATERIAL CONTAINING UV ABSORBER

[75] Inventors: David G. Leppard, Marly; Vien V. Toan, Lentigny; Mario Slongo, Tafers, all of Switzerland

[73] Assignee: Ciba-Geigy Corporation, Ardsley, N.Y.

[21] Appl. No.: 939,507

[22] Filed: Sep. 1, 1992

[30] Foreign Application Priority Data

Sep. 5, 1991 [CH] Switzerland .................. 2607/91

[51] Int. Cl.$^5$ .................................. G03C 1/46
[52] U.S. Cl. ..................... 430/507; 430/512; 430/931; 252/589
[58] Field of Search .................. 430/507, 512, 931; 252/589

[56] References Cited

U.S. PATENT DOCUMENTS

| 3,118,887 | 1/1964 | Hardy et al. | 252/589 |
| 3,244,708 | 4/1966 | Duennenberger et al. | 252/589 |
| 3,249,608 | 5/1966 | Biland et al. | 544/216 |
| 3,423,360 | 1/1969 | Huber et al. | 526/261 |
| 3,843,371 | 10/1974 | Piller et al. | 430/512 |
| 4,518,686 | 5/1985 | Sasaki et al. | 430/512 |
| 4,619,956 | 10/1986 | Susi | 524/87 |
| 4,790,959 | 12/1988 | Sasaki et al. | 430/512 |
| 4,812,498 | 3/1989 | Nakahara et al. | 524/91 |
| 4,853,471 | 8/1989 | Rody et al. | 548/261 |
| 4,921,966 | 5/1990 | Stegmann et al. | 548/260 |
| 4,973,701 | 11/1990 | Winter et al. | 548/260 |
| 4,973,702 | 11/1990 | Rody et al. | 548/261 |
| 5,032,498 | 7/1991 | Rody et al. | 430/512 |
| 5,084,375 | 1/1992 | Umemoto et al. | 430/512 |

FOREIGN PATENT DOCUMENTS

| 0764622 | 3/1971 | Belgium | 430/512 |
| 0200190 | 1/1988 | European Pat. Off. | |
| 0484695 | 1/1970 | Switzerland | |

OTHER PUBLICATIONS

WPI Acc. No.: 70-23529R/14.

Primary Examiner—Charles L. Bowers, Jr.
Assistant Examiner—Thomas R. Neville
Attorney, Agent, or Firm—Luther A. R. Hall

[57] ABSTRACT

A photographic material is described which comprises, on a base, blue-sensitive, green-sensitive and/or red-sensitive silver-halide emulsion layers and, if desired, a protection layer, a layer containing a UV absorber being arranged between the uppermost silver-halide emulsion layer and the protection layer, or on top of the uppermost silver-halide emulsion layer, wherein the UV absorber conforms to the formula

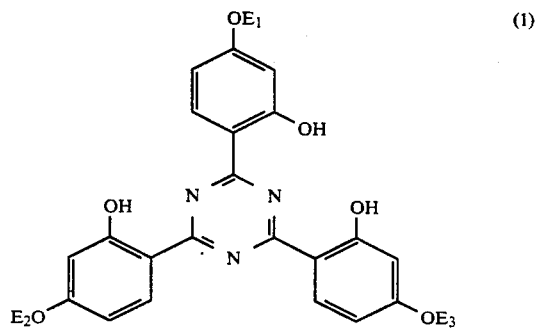

(1)

in which the radicals $E_1$, $E_2$ and $E_3$ are independently alkyl, substituted alkyl, alkenyl, glycidyl, cycloalkyl, phenylalkyl or siloxyl.

22 Claims, No Drawings

PHOTOGRAPHIC MATERIAL CONTAINING UV ABSORBER

The present invention relates to a novel photographic material which contains a UV absorber, in particular of the tris-2-hydroxyphenyltriazinyl type.

The hydroxyphenylbenzotriazoles used hitherto as UV absorbers in photographic materials have the disadvantage of inadequate inherent light stability. For this reason, the effectiveness of these UV absorbers decreases with increasing exposure. Furthermore, poor chemical stability, low solubility, an excessive inherent colour or an inadequate extinction coefficient of the triazines have in many cases prevented their use in photographic materials.

A group of triazine UV absorbers has now been found which, surprisingly, is substantially free from these disadvantages. They have improved inherent light stability and have the property of protecting image dyes and colour couplers better against the action of light than was possible using the hydroxyphenylbenzotriazoles and triazines usually used in photographic materials. In particular, the stability of the magenta and cyan layers in photographic materials can be increased by, for example, including this group of triazines in layers arranged above the magenta or cyan layer or including them directly in the cyan layer. Furthermore, these triazines can advantageously be combined with UV absorbers of the hydroxyphenylbenzotriazole type, in particular in the case of representatives thereof which are liquid at room temperature (cf., for example, U.S. Pat. No. 4,853,471, U.S. Pat. No. 4,973,702, U.S. Pat. No. 4,921,966 and U.S. Pat. No. 4,973,701). Such combinations allow a significant reduction in the amount of oil necessary for incorporating the UV absorbers into the photographic layer in question. This results in a low layer thickness or, if the layer thickness is kept constant, a greater concentration of UV absorber.

Combinations of the triazines with UV absorbers of other types, such as benzophenonones, oxanilides, cyanoacrylates, salicylates, acrylonitriles or thiazolines, are also suitable for use in photographic materials.

In particular photographic materials similar to those described in U.S. Pat. No. 4,518,686 can be successfully stabilised.

The present invention thus relates to a photographic material comprising, on a base, blue-sensitive, green-sensitive and/or red-sensitive silver-halide emulsion layers and, if desired, a protection layer, a layer containing a UV absorber being arranged between the uppermost silver-halide emulsion layer and the protection layer, or on top of the uppermost silver-halide layer, wherein the UV absorber conforms to the formula

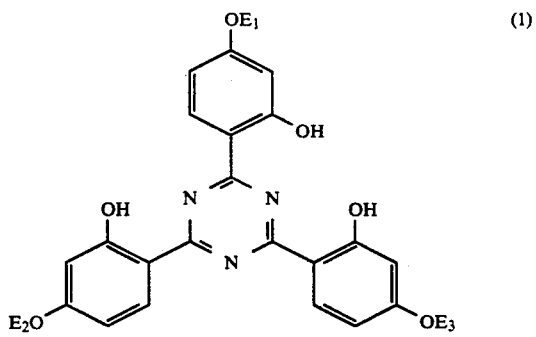
(1)

in which the radicals $E_1$, $E_2$ and $E_3$, independently of one another, are alkyl having 1 to 18 carbon atoms, alkyl having 1 to 18 carbon atoms and substituted by hydroxyl, alkenoxy having 2 to 18 carbon atoms, $—CO_2H$, $—CO_2R_2$ and/or $—O—COR_3$, oxygen-interrupted alkyl or hydroxyalkyl or glycidyloxyalkyl having 3 to 50 carbon atoms, alkenyl having 3 to 6 carbon atoms, glycidyl, a group of the formula

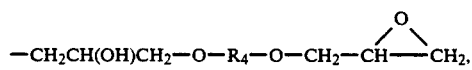

cyclopentyl, cyclohexy, phenylalkyl having 1 to 5 carbon atoms in the alkyl moiety, $—COR_5$, $—SO_2R_6$ or $—CH_2CH(OH)R_7$, where $R_2$ is alkyl having 1 to 18 carbon atoms, or oxygen-, sulfur- or nitrogen-interrupted alkyl or hydroxyalkyl having 3 to 30 carbon atoms, hydroxyalkyl having 2 to 18 carbon atoms, alkenyl having 3 to 18 carbon atoms, glycidyl, cycloalkyl having 5 to 8 carbon atoms, benzyl, alkylphenyl having 1 to 12 carbon atoms in the alkyl moiety, phenyl, furfuryl or a radical of the formula $—CH_2CH(OH)R_7$, $R_3$ is alkyl having 1 to 18 carbon atoms, alkenyl having 2 to 18 carbon atoms or phenyl, $R_4$ is alkylene having 2 to 10 carbon atoms, phenylene or a group of the formula

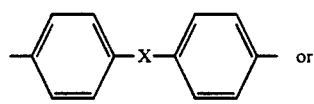 or

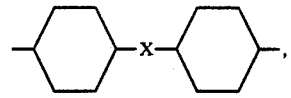, $R_5$ is alkyl having 1 to 18 carbon atoms, alkenyl having 2 to 18 carbon atoms or phenyl, $R_6$ is alkyl having 1 to 12 carbon atoms, phenyl, naphthyl or alkylphenyl having 1 to 18 carbon atoms in the alkyl moiety, and $R_7$ is phenylalkyl having 1 to 6 carbon atoms in the alkyl moiety or a radical of the formula $—CH_2OR_8$, where X is $—O—$, $—S—$, $—SO_2—$, $—CH_2—$ or $—C(CH_3)_2—$ and $R_8$ is cyclohexyl, benzyl, phenyl or tolyl, or the radicals $E_1$, $E_2$ and $E_3$, independently of one another, are radicals of the formula $—CH_2—CH(OR_x)R_y$, $—CH_2CH(OR_x)CH_2OR_z$,

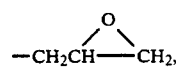

—$CH_2COR_y$ or —$CH_2COCH_2OR_z$, where $R_x$ is H, —$COR_s$, —$COOR_w$ or —$SiR_pR_qR_r$, $R_y$ is $C_1$-$C_{18}$alkyl or phenyl-$C_1$-$C_4$alkyl, $R_z$ is $C_1$-$C_{18}$alkyl, $C_2$-$C_{18}$alkenyl, phenyl-$C_1$-$C_4$alkyl, —$COR_s$ or oxygen-interrupted $C_2$-$C_{24}$alkyl or $C_2$-$C_{24}$hydroxyalkyl, $R_s$ is $C_1$-$C_{18}$alkyl, $C_2$-$C_{18}$alkenyl or phenyl, $R_w$ is $C_1$-$C_4$alkyl and $R_p$, $R_q$ and $R_r$, independently of one another, are $C_1$-$C_6$alkyl or phenyl; or the radical $E_1$, $E_2$ and $E_3$, independently of one another, are G-II groups, where II is a group of the formula

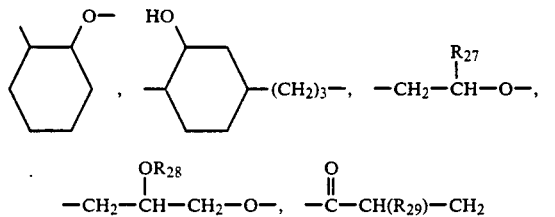 (II)

and G is a direct bond or a divalent group of one of the following formulae: —$(CH_2)_q$—, —$(CH_2)_q$—O—, —$(CH_2)_q$—O—$R_{26}$—, —$(CH_2)_q$—CO—X—$(CH_2)_r$—, —$(CH_2)_q$—CO—X—$(CH_2)_r$—O—,

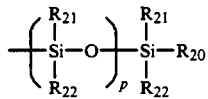, 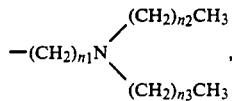, —$CH_2$—$\overset{R_{27}}{\underset{|}{CH}}$—O—,

—$CH_2$—$\overset{OR_{28}}{\underset{|}{CH}}$—$CH_2$—O—, —$\overset{O}{\overset{\|}{C}}$—$CH(R_{29})$—$CH_2$ or —$CH_2$—$CH(OH)$—$CH_2$—Y—$(CH_2)_q$—, in which q and r, independently of one another, are 1–4 and p is 0–50, $R_{26}$ is $C_1$-$C_{12}$alkylene, cyclohexylene or phenylene, $R_{27}$ is $C_1$-$C_{12}$alkyl, $C_5$-$C_8$cycloalkyl, phenyl, $C_2$-$C_{13}$alkoxymethyl, $C_6$-$C_9$cycloalkoxymethyl or phenoxymethyl, $R_{28}$ is a group of the formula G-II, $R_{29}$ is hydrogen or methyl, X is —O— or —$NR_{23}$—, in which $R_{23}$ is hydrogen, $C_1$-$C_{12}$alkyl or a —$(CH_2)_3$—G-II or —$(CH_2)_3$—O—G-II group, Y is —O— or —NH—, and $R_{20}$, $R_{21}$ and $R_{22}$, independently or one another, are $C_1$-$C_{18}$alkyl, cyclohexyl, phenyl or $C_1$-$C_{18}$alkoxy.

Suitable alkyl substituents having 1 to 18 carbon atoms in the compounds of the formula (1) are radicals such as methyl, ethyl, propyl, butyl, pentyl, hexyl, heptyl, octyl, nonyl, decyl, undecyl, dodecyl, tetradecyl, hexadecyl and octadecyl, and the corresponding branched isomers. Examples of alkyl radicals having 3 to 50 carbon atoms which are interrupted by oxygen, sulfur or nitrogen are, for example, —$(CH_2CH_2O)_{\overline{1-24}}$$CH_3$, —$(CH_2(CH_2S)_{\overline{1-24}}CH_3$, —$(CH_2CH_2NH)_{\overline{1-24}}CH_3$, —$(CH_2CH_2O)_{\overline{1-24}}CH_2CH_3$, —$(CH_2CH_2S)_{\overline{1-24}}CH_2CH_3$ and —$(CH_2CH_2NH)_{\overline{1-24}}CH_2CH_3$. Alkenyl radicals having 2 to 18 carbon atoms may be monounsaturated or, from 4 carbon atoms, polyunsaturated. Dialkylaminoalkyl radicals having a total of 4 to 16 carbon atoms may be represented, for example, by the formula —$(CH_2)_{n1}N\underset{(CH_2)_{n3}CH_3}{\overset{(CH_2)_{n2}CH_3}{\diagup}}$, where the sum of $n_1$, $n_2$ and $n_3$ is 4 to 16. Alkylene radicals having 2 to 10 carbon atoms may be derived from corresponding alkyl radicals. Oxygen-interrupted alkylene radicals having 4 to 50 carbon atoms may conform, for example, to the formula —$(CH_2CH_2O)_{\overline{1-24}}CH_2CH_2$.

Preference is given to compounds of the formula (1) in which the radicals $E_1$, $E_2$ and $E_3$, independently of one another, are radicals of the formula —$CH_2$—$CH(OR_x)R_y$, —$CH_2CH(OR_x)CH_2OR_z$,

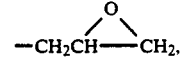

—$CH_2COR_y$ or —$CH_2COCH_2OR_z$, where $R_x$ is H, —$COR_s$, —$COOR_w$ or —$SiR_pR_qR_r$, $R_y$ is $C_1$-$C_{18}$alkyl or phenyl-$C_1$-$C_4$alkyl, $R_z$ is $C_1$-$C_{18}$alkyl, $C_2$-$C_{18}$alkenyl, phenyl-$C_1$-$C_4$alkyl, —$COR_s$ or oxygen-interrupted $C_2$-$C_{24}$alkyl or $C_2$-$C_{24}$hydroxyalkyl, $R_s$ is $C_1$-$C_{18}$alkyl, $C_2$-$C_{18}$alkenyl or phenyl, $R_w$ is $C_1$-$C_4$alkyl and $R_p$, $R_q$ and $R_r$, independently of one another, are $C_1$-$C_6$alkyl or phenyl; or the radicals $E_1$, $E_2$ and $E_3$, independently of one another, are G-II groups, where II is a group of the formula

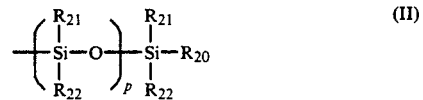 (II)

and G is a direct bond or a divalent group of one of the following formulae:

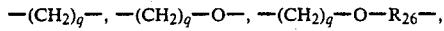

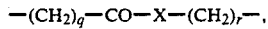

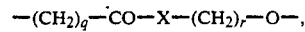

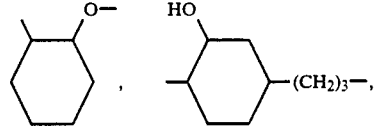

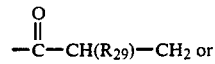

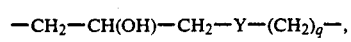

—$CH_2$—$CH(OH)$—$CH_2$—Y—$(CH_2)_q$—, in which q and r, independently of one another, are 1–4 and p is 0–50, $R_{26}$ is $C_1$-$C_{12}$alkylene, cyclohexylene or phenylene, $R_{27}$ is $C_1$-$C_{12}$alkyl, $C_5$-$C_8$cycloalkyl, phenyl, $C_2$-$C_{13}$alkoxymethyl, $C_6$-$C_9$cycloalkoxymethyl or phenoxymethyl, $R_{28}$ is a group of the formula G-II, $R_{29}$ is hydrogen or methyl, X is —O— or —$NR_{23}$—, in which $R_{23}$ is hydrogen, $C_1$-$C_{12}$alkyl or a —$(CH_2)_3$—G-II or —$(CH_2)_3$—O—G-II group, Y is —O— or —NH—, and $R_{20}$, $R_{21}$, and $R_{22}$, independently of one another, are $C_1$-$C_{18}$alkyl, cyclohexyl, phenyl or $C_1$-$C_{18}$alkoxy.

Preference is furthermore given to compounds of the formula (1) in which the radicals $E_1$, $E_2$ and $E_3$, independently of one another, are radicals of the formula —$CH_2$—$CH(OR_x)R_y$, —$CH_2CH(OR_x)CH_2OR_z$, —$CH_2COR_y$ or —$CH_2COCH_2OR_z$, where $R_x$ is H, —$COR_s$, —$COOR_w$ or —$SiR_pR_qR_r$, $R_y$ is $C_1$-$C_8$alkyl, $R_z$ is $C_1$-$C_{18}$alkyl, $C_2$-$C_{18}$alkenyl, benzyl, —$COR_s$ or oxygen-interrupted $C_2$-$C_{24}$alkyl or $C_2$-$C_{24}$hydroxyalkyl, $R_s$ is $C_1$-$C_{18}$alkyl, $C_2$-$C_{18}$alkenyl or phenyl, $R_w$ is $C_1$-$C_4$alkyl, and $R_p$, $R_q$ and $R_r$, independently of one another, are $C_1$-$C_6$alkyl; or $E_1$, $E_2$ and $E_3$ are a G-II group, where II is a group of the formula

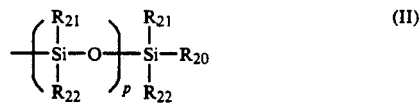

and G is a direct bond or a divalent group of one of the following formulae: $-(CH_2)_q-$, $-(CH_2)_q-O-$, $-(CH_2)_q-CO-X-(CH_2)_r-$,

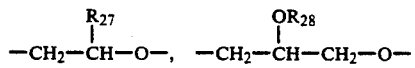

or $-CH_2-CH(OH)-CH_2-Y-(CH_2)_q-$, in which q and r, independently of one another, are 1, 2 or 3 and p is 0-50, $R_{27}$ is methyl, phenyl, $C_3$-$C_9$alkoxymethyl or phenoxymethyl, $R_{28}$ is a group of the formula G-II, X and Y are $-O-$, $R_{20}$, $R_{21}$ and $R_{22}$, independently of one another, are $C_1$-$C_8$alkyl, phenyl or $C_1$-$C_8$alkoxy.

Particular preference is given to compounds of the formula (1) in which the radicals $E_1$, $E_2$ and $E_3$, independently of one another, are radicals of the formula $-CH_2-CH(OR_x)R_y$ or $-CH_2CH(OR_x)CH_2OR_z$, where $R_x$ is H, $-COR_s$, $-COOCH_3$ or $Si(CH_3)_2R_r$, $R_y$ is $C_1$-$C_8$alkyl, $R_z$ is $C_1$-$C_{18}$alkyl, $C_2$-$C_{18}$alkenyl, $-COR_s$ or oxygen-interrupted $C_2$-$C_{24}$alkyl or $C_2$-$C_{24}$hydroxyalkyl, $R_s$ is $C_1$-$C_4$alkyl or $C_2$-$C_4$alkenyl and $R_r$ is $C_1$-$C_6$alkyl; or $R_1$ is a G-II group, where II is a group of the formula

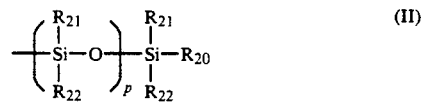

and p is 0, G is a divalent group of one of the following formulae: $-(CH_2)_3-$, $-(CH_2)_2-O-$, $-CH_2-CO-O-CH_2-$, $-CH_2-CH(CH_2-O-C_4H_9)-O-$,

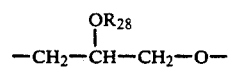

or $-CH_2-CH(OH)-CH_2-O-(CH_2)_3-$, $R_{28}$ is $-Si(CH_3)_2R_{22}$, $R_{20}$ and $R_{21}$, independently of one another, are methyl or ethyl, and $R_{22}$ is $C_1$-$C_8$alkyl.

Very particular preference is given to compounds of the formula (1) in which the radicals $E_1$, $E_2$ and $E_3$, independently of one another, are radicals of the formula $-CH_2CH(OR_x)CH_2OR_z$, where $R_x$ is H, $-COR_s$, $-COOCH_3$ or $-Si(CH_3)_2R_r$, $R_z$ is $C_1$-$C_{18}$alkyl, $C_2$-$C_{18}$alkenyl, $-COR_s$ or oxygen-interrupted $C_1$-$C_{24}$alkyl or $C_2$-$C_{24}$hydroxyalkyl, $R_s$ is $C_1$-$C_4$alkyl or $C_2$-$C_4$alkenyl and $R_r$ is $C_1$-$C_6$alkyl.

The material according to the invention preferably contains gelatin intermediate layers between the silver-halide emulsion layers.

In a further preferred embodiment, the material according to the invention contains a further layer containing a UV absorber of the formula (1), arranged between the green-sensitive and red-sensitive silver-halide emulsion layers.

Good results are also achieved if the UV absorber of the formula (1) is additionally present in the red-sensitive silver-halide emulsion layer.

In the layer between the green-sensitive and red-sensitive layers and/or in the red-sensitive layer, it is advantageous to use benzotriazole compounds in place of the UV absorbers of the formula (1).

These benzotriazole compounds preferably conform to the formula

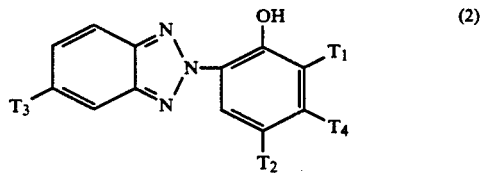

in which $T_1$, $T_2$ and $T_3$, independently of one another, are hydrogen, halogen, alkyl, carboxylate-substituted alkyl, alkoxy, aryloxy, hydroxyl or acyloxy, and $T_4$ is hydrogen, alkoxy, aryloxy or acyloxy.

Particular preference is given to compounds of the formula (2) which are liquid at room temperature.

In a further aspect, the present invention also relates to a photographic material comprising, on a base, blue-sensitive, green-sensitive and/or red-sensitive silver-halide emulsion layers and a protection layer, a layer containing a UV absorber being arranged between the uppermost silver-halide emulsion layer and the protection layer, wherein (a) the UV absorber conforms to the formula

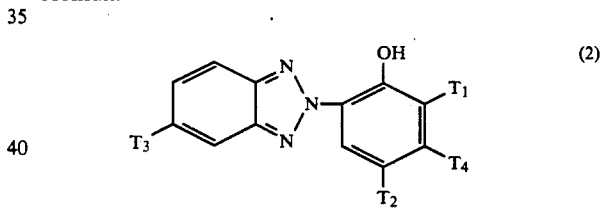

in which $T_1$, $T_2$ and $T_3$, independently of one another, are hydrogen, halogen, alkyl, carboxylate-substituted alkyl, alkoxy, aryloxy, hydroxyl or acyloxy, and $T_4$ is hydrogen, alkoxy, aryloxy or acyloxy, and (b) the material contains at least one further layer containing a UV absorber of the formula (1).

The further layer is preferably arranged between the green-sensitive and red-sensitive silver-halide emulsion layers.

In a further preferred embodiment, the photographic material additionally contains a UV absorber of the formula (1) in the red-sensitive layer. It may furthermore be advantageous for the UV absorber of the formula (1) in the further layer or in the red-sensitive layer to be replaced by a UV absorber of the formula (2); in this case, however, at least one layer must contain a UV absorber of the formula (1).

Preferred photographic materials contain gelatin intermediate layers between the silver-halide emulsion layers.

In a further embodiment of the present invention, the photographic material comprises, on a base, at least two silver-halide emulsion layers with a UV absorber-containing layer between these layers, wherein the UV absorber conforms to the formula (1). The two silver-halide emulsion layers are preferably green-sensitive and red-sensitive silver-halide emulsion layers. Preference is furthermore given to a corresponding material in which, in addition, the red-sensitive silver-halide emulsion layer contains a UV absorber of the formula (1) or (2).

A further embodiment of the present invention relates to a photographic material which comprises, on a base, a red-sensitive silver-halide emulsion layer and, if desired, blue-sensitive and/or green-sensitive silver-halide emulsion layers, wherein the red-sensitive silver-halide emulsion layer contains a UV absorber of the formula (1). It preferably contains a layer containing a UV absorber of the formula (2) between the red-sensitive silver-halide emulsion layer and the base.

It may furthermore be advantageous for all or some of said layers which may contain a UV absorber to contain a mixture of the UV absorbers of the formulae (1) and (2).

The photographic materials according to the invention have the advantage over materials containing benzotriazole UV absorbers that the UV absorbers of the formula (1) are required in a comparatively small amount in order to ensure adequate protection against UV radiation. This means that the thickness of the layers containing the UV absorbers of the formula (1) can be very thin, which has a positive effect, for example, on the sharpness of the images produced by means of this material. Obviously, the use of a comparable amount of UV absorber gives even better protection.

Typical and preferred compounds of the formula (1) are shown in the table below:

TABLE 1

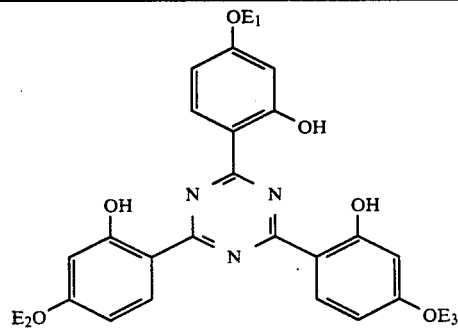

(1a)

| Comp. No. | $E_1$, $E_2$, $E_3$ |
|---|---|
| (3) | $-CH_2CH(OH)CH_2OC_4H_9$ |
| (4) | $-CH_2CH(OH)CH_2OCH_2CHCH(C_2H_5)C_4H_9$ |
| (5) | $-C_8H_{17}$ |
| (6) | $-CH_2COOCH_3$ |
| (7) | $-CH_2CH(OH)CH_2OC_8H_{17}/C_{10}H_{21}$ |
| (8) | $-CH_2CH(OH)CH_2OC_6H_{13}$ |
| (9) | $-CH_2CH(OH)CH_2-C_6H_5$ |
| (10) | $-CH_2CO-OC_{18}H_{35}$ |
| (11) | $-CH_2CO-OCH_2CH(C_2H_5)C_4H_9$ |
| (12) | $-(CH_2)_3CO-OC_2H_5$ |
| (13) | $-C_4H_9$ |
| (14) | $-CH_2CH(OH)CH_2OC(CH_3)_3$ |
| (15) | $-CH_2CH(OH)CH_2OCH(CH_3)_2$ |
| (16) | $-CH_2CH(OH)CH_2OC_{12}H_{25}/C_{14}H_{29}$ |
| (17) | $-CH_2CH(OH)CH_2OC_{13}H_{27}/C_{15}H_{38}$ |
| (18) | $-CH_2CH(OH)CH_2OCH_2CH=CH_2$ |
| (19) | $-CH_2CH(OCOCH_3)CH_2OC_4H_9$ |
| (20) | $-CH_2CH(OCOCH_3)CH_2OCH_2CH(C_2H_5)C_4H_9$ |
| (21) | $-CH_2CH(OCOOCH_3)CH_2OC_4H_9$ |
| (22) | $\overset{O}{\underset{\|}{CH_2CCH_2OC_4H_9}}$ |
| (23) | $-\underset{CH_2OC_4H_9}{\overset{\|}{CH_2CHOSi(CH_3)_2[C(CH_3)_3]}}$ |
| (24) | $-\underset{CH_2OC_4H_9}{\overset{\|}{CH_2CHOSi(CH_3)_2[C(CH_3)_2CH(CH_3)_2]}}$ |
| (25) | $-CH_2CH_2CH_2Si(CH_3)_3$ |
| (26) | $-\underset{CH_2OC_2H_5}{\overset{\|}{CH_2CHOSi(CH_3)_2[C(CH_3)_3]}}$ |
| (27) | $-\underset{CH_2OC_2H_5}{\overset{\|}{CH_2CHOSi(CH_2)_2[C(CH_3)_2CH(CH_3)_2]}}$ |

TABLE 1-continued (1a)

[Structure: triazine with three 2-hydroxy-4-OE-phenyl groups, where substituents are OE₁, OE₂, OE₃]

| Comp. No. | E₁, E₂, E₃ |
|---|---|
| (28) | —CH₂CH(OH)CH₂OC₁₅H₃₁/C₁₇H₃₅ |
| (29) | —CH₂CH(OH)CH₂OC₄H₉/CH₂CH(C₂H₅)C₄H₉ |
| (30) | —CH₂CH(OH)CH₂OC₂H₅/C₄H₉ /CH₂CH(C₂H₅)C₄H₉ |
| (31) | —CH₂CH(OH)CH₂OC₄H₉/CH₂CH(CH₃)C₂H₅/CH₂CH(C₂H₅)C₄H₉ |
| (32) | CH₂CH(OH)CH₂OCH₂CH(CH₃)C₂H₅/CH₂CH(C₂H₅)C₄H₉ |
| (33) | —CH₂CH(OH)CH₂OCH(CH₃)₂/CH₂CH(C₂H₅)C₄H₉ |
| (34) | —CH₂CH[OSi(CH₃)₂[C(CH₃)₂CH(CH₃)₂]}CH₂OC₄H₉ |
| (35) | —CH₂CH[OSi(CH₃)₂[C(CH₃)₂CH(CH₃)₂]}CH₂OCH₂CH(C₂H₅)C₄H₉ |
| (36) | —CH₂CH{OSi(CH₃)₂[C(CH₃)₃]}CH₂OC₄H₉ |
| (37) | —CH₂CH{OSi(CH₃)₂[C(CH₃)₂CH(CH₃)₂]}CH₂OC₄H₉/CH₂CH(C₂H₅)C₄H |
| (38) | —CH₂CH(OH)CH₂OC₃H₇ |

Examples of compounds of the formula (2) are:

[Structure: 2-(2H-benzotriazol-2-yl)phenol with substituents T₁, T₂, T₃, T₄]

| HBT-No. | T₁ | T₂ | T₃ |
|---|---|---|---|
| HBT-1 | H | CH₃ | H |
| HBT-2 | H | C(CH₃)₃ | H |
| HBT-3 | C(CH₃)₃ | CH₃ | Cl |
| HBT-4 | C(CH₃)₃ | C(CH₃)₃ | Cl |
| HBT-5 | C(CH₃)₂C₂H₅ | C(CH₃)₂C₂H₅ | H |
| HBT-6 | CH(CH₃)C₂H₅ | C(CH₃)₃ | H |
| HBT-7 | C(CH₃)₂—C₆H₅ | C(CH₃)₂—C₆H₅ | H |
| HBT-8 | C(CH₃)₃ | CH₂CH₂COOC₈H₁₇ (Isomers)* | Cl |
| HBT-9 | C(CH₃)₃ | CH₂CH₂COOC₈H₁₇ (Isomers)* | H |
| HBT-10 | C₁₂H₂₅ | CH₃ | H |

-continued

[Structure: isomeric benzotriazolyl phenol with T₁, T₃, T₄]

| HBT-No. | T₁ | T₂ | T₃ |
|---|---|---|---|
| | (Isomers)* | | |

*principal product

Yellow couplers which can be used in the material according to the invention are preferably compounds of the formula A $$R_1-CO-\underset{\underset{Q}{|}}{CH}-CO-NHR_2,\quad (A)$$

in which $R_1$ is alkyl or aryl, $R_2$ is aryl and Q is hydrogen or a group which can be eliminated by reaction with the oxidised developer.

A group of yellow couplers comprises the compounds of the formula A in which $R_1$ is t-butyl and $R_2$ is a group of the formula

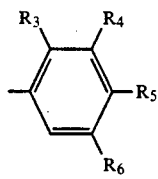

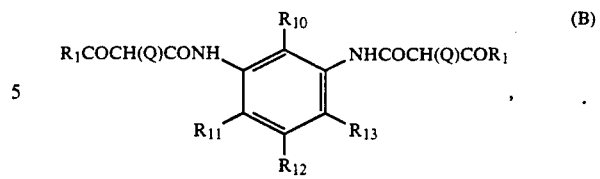

in which $R_3$ is hydrogen, halogen, alkyl or alkoxy, and $R_4$, $R_5$ and $R_6$ are hydrogen, halogen, alkyl, alkenyl, alkoxy, aryl, carboxyl, alkoxycarbonyl, carbamoyl, sulfonyl, sulfamoyl, alkoxysulfonylamino, acylamino, ureido or amino.

Preferably, $R_3$ is chlorine, $R_4$ and $R_5$ are hydrogen and $R_6$ is an acylamino group. This group also includes the compounds of the formula

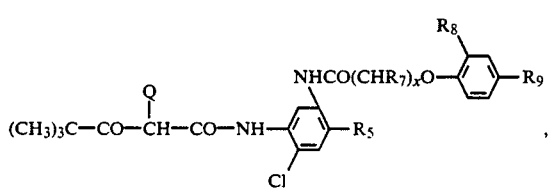

in which x is 0-4, $R_7$ is hydrogen or alkyl, $R_8$ and $R_9$ are alkyl.

Another group of yellow couplers conforms to the formula B in which $R_{10}$ is hydrogen, halogen or alkoxy, $R_{11}$, $R_{12}$ and $R_{13}$ are hydrogen, halogen, alkyl, alkenyl, alkoxy, aryl, carboxyl, alkoxycarbonyl, carbamoyl, sulfonyl, sulfamoyl, sulfonamido, acylamino, ureido or amino, and $R_1$ and Q are as defined above.

This group includes compounds of the formula B in which $R_1$ is t-butyl, $R_{10}$ is chlorine, $R_{11}$ and $R_{13}$ are hydrogen, and $R_{12}$ is alkoxycarbonyl.

In the compounds of the formulae A and B, leaving group Q may be hydrogen or a heterocyclic group

in which $R_{14}$ is a divalent organic group which supplements the ring to make up a 4–7-membered ring, or Q is an —$OR_{15}$ group in which $R_{15}$ is alkyl, aryl, acyl or a heterocyclic radical.

Typical examples of customary yellow couplers are the compounds of the formulae below:

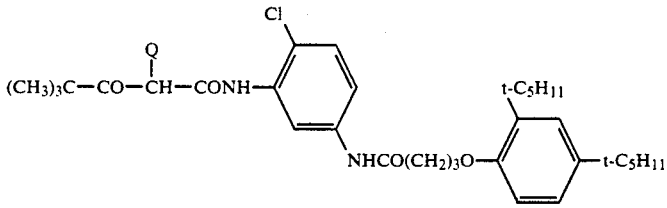

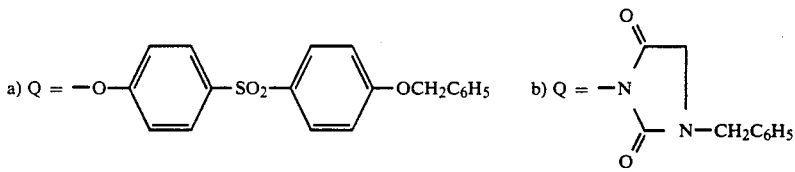

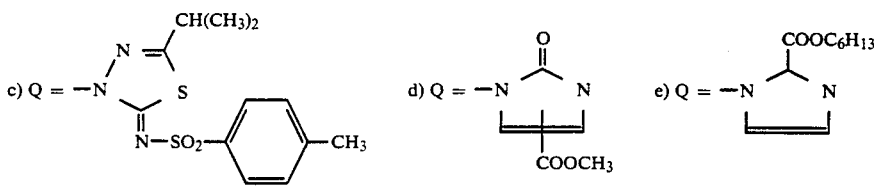

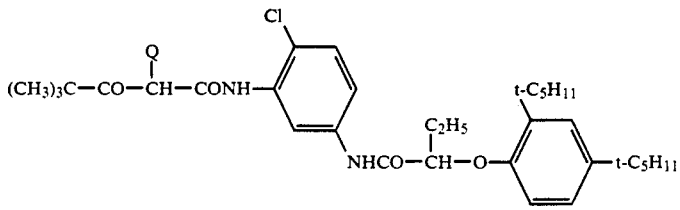

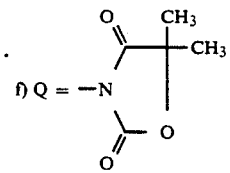 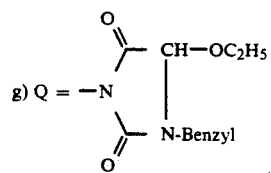
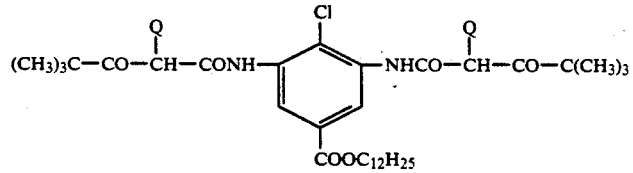
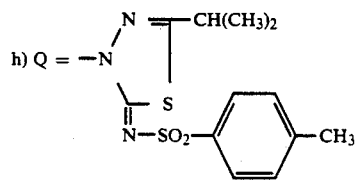
Further examples of yellow couplers are given in U.S. Pat. Nos. 2,407,210, 2,778,658, 2,875,057, 2,908,513, 2,908,573, 3,227,155, 3,227,550, 3,253,924, 3,265,506, 3,277,155, 3,408,194, 3,341,331, 3,369,895, 3,384,657, 3,415,652, 3,447,928, 3,551,155, 3,582,322, 3,725,072, 3,891,445, 3,933,501, 4,115,121, 4,401,752 and 4,022,620, in DE-A 1,547,868, 2,057,941, 2,162,899, 2,163,813, 2,213,461, 2,219,917, 2,261,361, 2,261,362, 2,263,875, 2,329,587, 2,414,006 and 2,422,812, in GB-A 1,425,020 and 1,077,874 and in JP-A-88/123 047 and in EP-A 447 969.
The yellow couplers are usually used in an amount of 0.05-2 mol and preferably 0.1-1 mol per mol of silver halide.
Typical and preferred yellow couplers conform to the formulae:
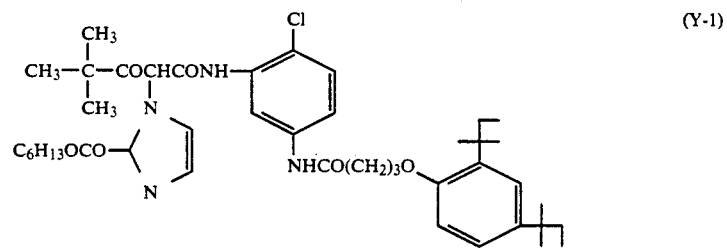
(Y-1)
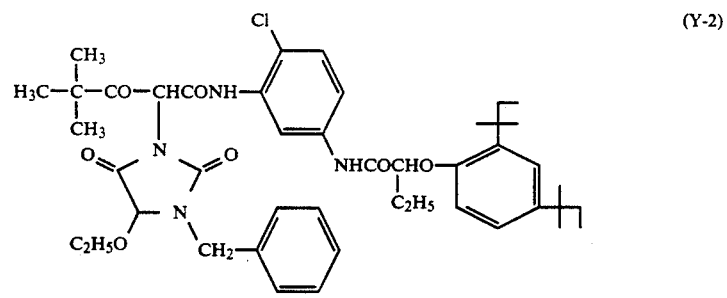
(Y-2)
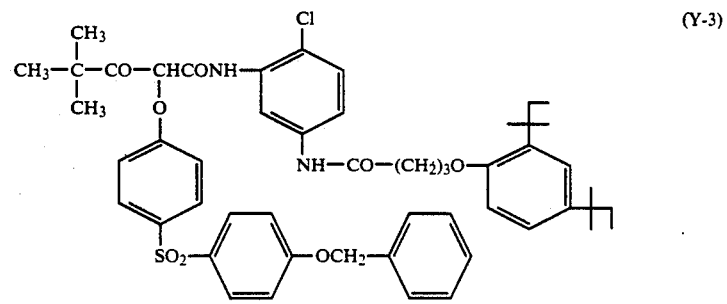
(Y-3)

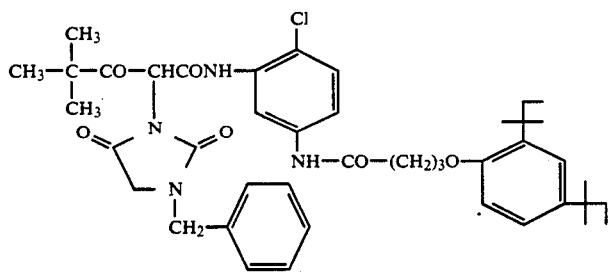
(Y-4)
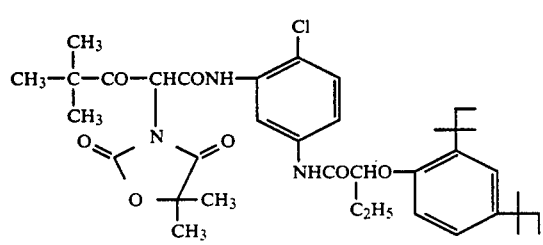
(Y-5)
$\boxed{\phantom{+}} = -C(CH_3)_2C_2H_5$
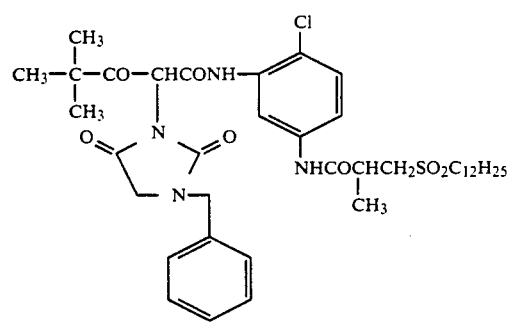
(Y-6)
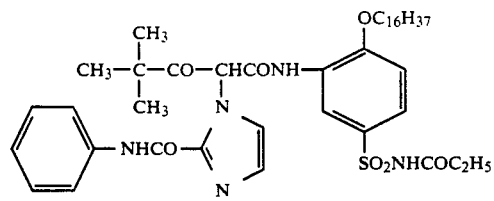
(Y-7)
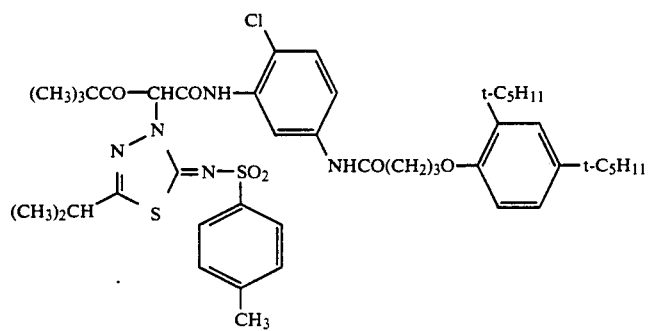
(Y-8)

-continued

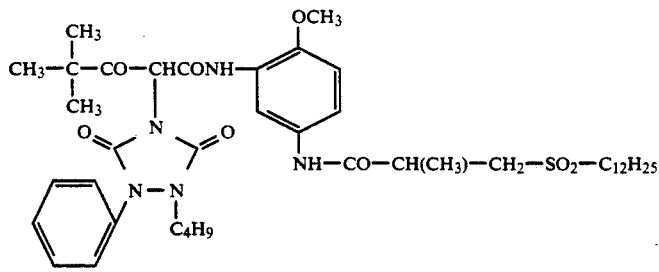
(Y-9)

Examples of magenta couplers may be simple 1-aryl-5-pyrazolones or pyrazole derivatives which have been condensed with 5-membered hetero rings, e.g. imidazopyrazoles, pyrazolopyrazoles, pyrazolotriazoles and pyrazolotetrazoles.

A group of magenta couplers comprises 5-pyrazolones of the formula C

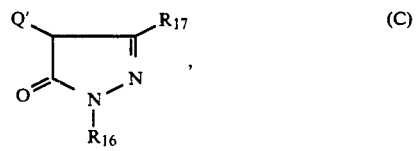
(C)

as described in British Patent 2 003 473. In this formula, $R_{16}$ is hydrogen, alkyl, aryl, alkenyl or a heterocyclic group. $R_{17}$ is hydrogen, alkyl, aryl, a heterocyclic group, an ester group, an alkoxy group, an alkylthio group, a carboxyl group, an arylamino group, an acylamino group, a (thio)urea group, a (thio)carbamoyl group, a guanidino group or a sulfonamido group.

$R_{17}$ is preferably an

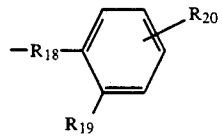

group, in which $R_{18}$ is imino, acylamino or ureido, $R_{19}$ is hydrogen, halogen, alkyl or alkoxy, $R_{20}$ is hydrogen, alkyl, acylamino, carbamoyl, sulfamoyl, sulfonamido, alkoxycarbonyl, acyloxy or a urethane group.

If Q' is hydrogen, the magenta coupler is tetraequivalent with respect to the silver halide.

Typical examples of magenta couplers of this type are compounds of the formula

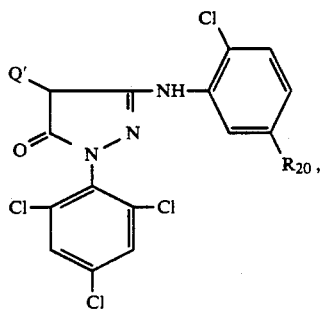

in which $R_{20}$ is as defined above, and Q', as described above, is a leaving group. These compounds are preferably present in the material according to the invention.

Further examples of tetraequivalent magenta couplers of this type are given in U.S. Pat. Nos. 2,983,608, 3,061,432, 3,062,653, 3,127,269, 3,152,896, 3,311,476, 3,419,391, 3,519,429, 3,558,319, 3,582,322, 3,615,506, 3,684,514, 3,834,908, 3,888,680, 3,891,445, 3,907,571, 3,928,044, 3,930,861, 3,930,866 and 3,933,500 and JP-A-89/309 058.

If Q' in the formula C is not hydrogen, but instead a group which is eliminated during the reaction with the oxidised developer, the magenta coupler is diequivalent. In this case, Q can be, for example, halogen or a group bonded to the pyrazole ring via O, S or N. Diequivalent couplers of this type give greater colour density and are more reactive towards the oxidised developer than are the corresponding tetraequivalent magenta couplers.

Examples of diequivalent magenta couplers are described in U.S. Pat. No. 3,006,579, 3,419,391, 3,311,476, 3,432,521, 3,214,437, 4,032,346, 3,701,783, 4,351,897, 3,227,554, in EP-A-133 503, DE-A-2 944 601, JP-A-78/34 044, 74/53 435, 74/53 436, 75/53 372 and 75/122 935.

Typical and preferred magenta couplers conform to the formulae:

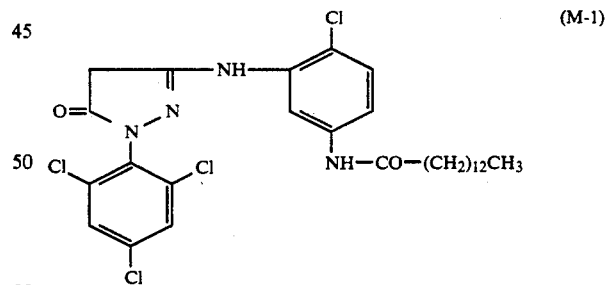
(M-1)

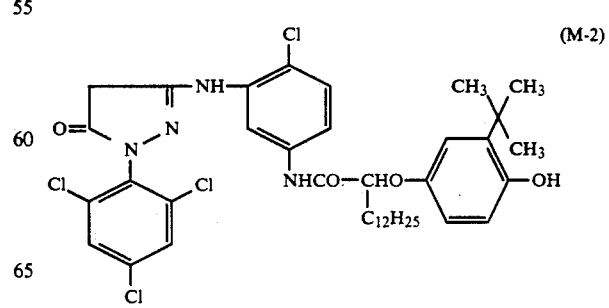
(M-2)

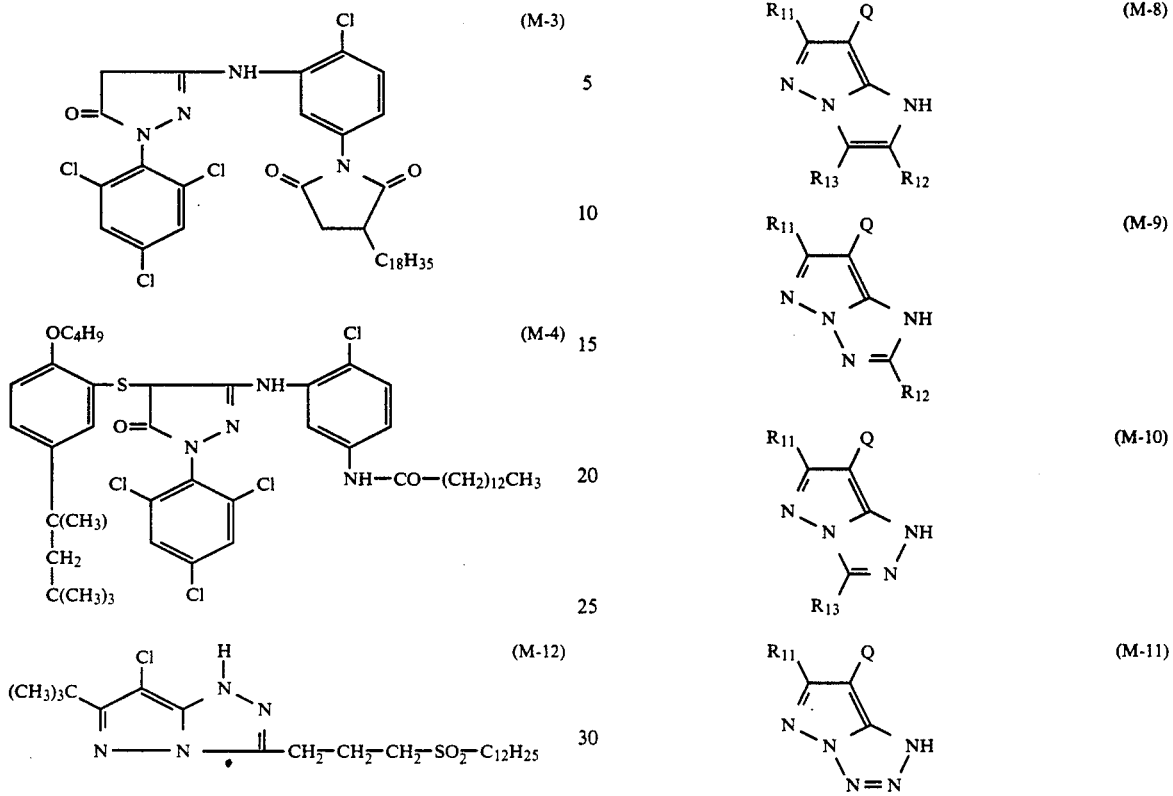

It is possible for 2 pyrazolone rings to be linked via a divalent Q′, giving so-called bis-couplers. These are described, for example, in U.S. Pat. No. 2,632,702, U.S. Pat. No. 2,618,864, GB-A-968 461, GB-A-786 859, JP-A-76/37 646, 59/4 086, 69/16 110, 69/26 589, 74/37 854 and 74/29 638. Y is preferably an O-alkoxyarylthio group.

As mentioned above, the magenta couplers used can also be pyrazoles condensed with 5-membered heterocyclic rings, known as pyrazoloazoles. Their advantages over simple pyrazoles is that they give dyes of greater formalin resistance and have purer absorption spectra.

Magenta couplers of the pyrazoloazole type, which are likewise preferred, may be represented by the formula

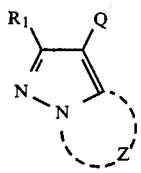

in which $R_1$ is hydrogen or a substituent, Z represents the non-metallic atoms necessary to complete a 5-membered ring containing 2 or 3 nitrogen atoms, it being possible for this ring to be substituted, and Q is hydrogen or a leaving group.

Of these compounds, preference is given to magenta couplers of the formulae $R_{11}$, $R_{12}$ and $R_{13}$, independently of one another, are, for example, hydrogen, halogen, —$CR_3$ in which the radicals R, independently of one another, are hydrogen or alkyl, aryl, heterocyclyl, cyano, hydroxyl, nitro, carboxyl, amino, alkoxy, aryloxy, acylamino, alkylamino, anilino, ureido, sulfamoylamino, alkylthio, arylthio, alkoxycarbonylamino, sulfonamido, carbamoyl, sulfamoyl, sulfonyl, alkoxycarbonyl, heterocyclylyloxy, azo, acyloxy, carbamoyloxy, silyloxy, aryloxycarbonylamino, imido, heterocyclylthio, sulfinyl, phosphonyl, aryloxycarbonyl, acyl or azolyl, preferably hydrogen; halogen (for example chlorine or bromine) —$CR_3$ in which the radicals $R_3$ are, independently of one another, hydrogen or alkyl, aralkyl, alkenyl, alkynyl, cycloalkyl or cycloalkenyl, particularly preferably methyl, ethyl, propyl, isopropyl, t-butyl, tridecyl, 2-methanesulfonylethyl, 3-(3-pentadecylphenoxy)propyl, 3-(4-(2-(4-(4-hydroxyphenylsulfonyl)phenoxy)-dodecanamido)phenyl)propyl, 2-ethoxytridecyl, trifluoromethyl, cyclopentyl, 3-(2,4-di-t-amylphenoxy)propyl; aryl (for example phenyl, 4-t-butylphenyl, 2,4-di-t-amylphenyl or 4-tetradecaneamidophenyl); heterocyclyl (for example 2-furyl, 2-thienyl, 2-pyrimidinyl or 2-benzothiazolyl); cyano; hydroxyl, nitro; carboxyl; amino; alkoxy (for example methoxy, ethoxy, 2-methoxyethoxy; 2-dodecylethoxy; 2-methanesulfonylethoxy); aryloxy (for example phenoxy, 2-methylphenoxy, 4-t-butylphenoxy, 3-nitrophenoxy, 3-t-butyloxycarbamoylphenoxy or 3-methoxycarbamoyl); acylamino (for example acetoamido, benzamido, tetradecaneamido, 2-(2,4-di-t-amylphenoxy)butaneamido, 4-(3-t-butyl-4-hydroxyphenoxy)butaneamido, 2-(4-(4-hydroxyphenylsulfonyl)phenoxy)decaneamido or methylbutylamino); anilino (for example phenylamino, 2-chloroanilino, 2-chloro-5-tetradecaneaminoanilino, 2-chloro-5- dodecyloxycarbonylanilino, N-acetylanilino, 2-chloro-5-(alpha-(3-t-butyl-4-hydroxyphenoxy)-dodecaneamidoanilino)); ureido (for example phenylureido, methylureido or N,N-dibutylureido); sulfamoylamino (for example N,N-dipropylsulfamoylamino or N-methyl-N-decylsulfamoylamino); alkylhio (for example methylthio, octylthio, tetradecylthio, 2-phenoxyethylthio, 3-phenoxypropylthio or 3-(4-t-butylphenoxy)propylthio); arylthio (for example phenylthio, 2-butoxy-5-t-octylphenylthio, 3-pentadecylphenylthio, 2-carboxyphenylthio or 4-tetradecaneamidophenylthio); alkoxycarbonylamino (for example methoxycarbonylamino or tetradecyloxycarbonylamino); sulfonamido (for example methanesulfonamido, hexadecanesulfonamido, benzenesulfonamido, p-toluenesulfonamido, octadecanesulfonamido or 2-methoxy-5-t-butylbenzenesulfonamido); carbamoyl (for example N-ethylcarbamoyl, N,N-dibutylcarbamoyl, N-(2-dodecyloxyethyl)-carbamoyl, N-methyl-N-dodecylcarbamoyl or N-(3-(2,4-di-t-amylphenoxy)-propyl)-carbamoyl); sulfamoyl (for example N-ethylsulfamoyl, N,N-dipropylsulfamoyl, N-2-(dodecyloxyethyl)sulfamoyl, N-ethyl-N-dodecylsulfamoyl or N,N-diethylsulfamoyl); sulfonyl (for example methanesulfonyl, octanesulfonyl, benzenesulfonyl or toluenesulfonyl); alkoxycarbonyl (for example methoxycarbonyl, butoxycarbonyl, dodecyloxycarbonyl or octadecyloxycarbonyl); heterocyclyloxy (for example 1-phenyltetrazol-5-oxy or 2-tetrahydropyranyloxy); azo (for example phenylazo, 4-methoxyphenylazo, 4-pivaloylaminophenylazo or 2-hydroxy-4-propanoylphenylazo); acyloxy (for example acetoxy); carbamoyloxy (for example N-methylcarbamoyloxy or N-phenylcarbamoyloxy); silyloxy (for example trimethylsilyloxy or dibutylmethylsilyloxy); aryloxycarbonylamino (for example phenoxycarbonylamino); imido (for example N-succinimido, N-phthalimido or 3-octadecenylsuccinimido); heterocyclylthio (for example 2-benzothiazolylthio, 2,4-diphenyloxy-1,3,5-triazole-6-thio or 2-pyridylthio); sulfinyl (for example dodecanesulfinyl, 3-pentadecylphenylsulfinyl or 3-phenoxypropylsulfinyl); phosphonyl (for example phenoxyphosphonyl, octyloxyphosphonyl or phenylphosphonyl); aryloxycarbonyl (for example phenoxycarbonyl); acyl (for example acetyl, 3-phenylpropanoyl, benzoyl or 4-dodecyloxybenzoyl); or azolyl (for example imidazolyl, pyrazolyl or 3-chloropyrazol-1-yl).

These substituents may be further substituted, for example by halogen or by an organic radical bonded via a C, O, N or S atom.

Preferred groups $R_{11}$ are alkyl, aryl, alkoxy, aryloxy, alkylthio, ureido, urethane and acylamino groups.

$R_{12}$ may be as defined for $R_{11}$ and is preferably hydrogen, alkyl, aryl, a heterocyclic ring, alkoxycarbonyl, carbamoyl, sulfamoyl, sulfinyl, acyl or cyano.

$R_{13}$ may be as defined for $R_{11}$ and is preferably hydrogen, alkyl, aryl, a heterocyclic ring, alkoxy, aryloxy, alkylthio, arylthio, alkoxycarbonyl, carbamoyl or acyl, in particular alkyl, aryl, a heterocyclic ring, alkylthio or arylthio.

Q is hydrogen or a leaving group, such as halogen, alkoxy, aryloxy, acyloxy, alkyl- or arylsulfonyloxy, acylamino, alkyl- or arylsulfonamido, alkoxycarbonyloxy, aryloxycarbonyloxy, alkyl-, aryl- or heterocyclyl-S-carbamoylamino, a 5- or 6-membered, nitrogen-containing heterocyclic radical, imido or Arylazo. These groups may be further substituted as indicated for $R_{11}$.

Q is preferably halogen (for example fluorine, chlorine or bromine); alkoxy (for example ethoxy, dodecyloxy, methoxyethylcarbamoylmethoxy, carboxypropoxy, methylsulfonylethoxy or ethoxycarbonylmethoxy); aryloxy (for example 4-methylphenoxy, 4-chlorophenoxy, 4-methoxyphenoxy, 4-carboxyphenoxy, 3-ethoxycarboxyphenoxy, 3-acetylaminophenoxy or 2-carboxyphenoxy); acyloxy (for example acetoxy, tetradecanoyloxy or benzoyloxy); alkyl- or arylsulfonyloxy (for example methanesulfonyloxy or toluenesulfonyloxy); acylamino (for example dichloroacetylamino or heptafluorobutyrylamino); alkyl- or arylsulfonamido (for example methanesulfonamido, trifluoromethanesulfonamido or p-toluenesulfonamido); alkoxycarbonyloxy (for example ethoxycarbonyloxy or benzyloxycarbonyloxy); aryloxycarbonyloxy (for example phenoxycarbonyloxy); alkyl-, aryl- or heterocyclyl-S- (for example dodecylthio, 1-carboxydodecylthio, phenylthio, 2-butoxy-5-t-octylphenylthio or tetrazolylthio); carbamoylamino (for example N-methylcarbamoylamino or N-phenylcarbamoylamino); a 5- or 6-membered, nitrogen-containing ring (for example imidazolyl, pyrazolyl, triazolyl, tetrazolyl or 1,2-dihydro-2-oxo-1-pyridyl); imido (for example succinimido or hydantoinyl); or arylazo (for example phenylazo or 4-methoxyphenylazo).

Q may alternatively form corresponding bis-compounds by condensation of 4 equivalents of coupler with an aldehyde or ketone. Furthermore, Q may contain photographically active groups, such as development inhibitors or development accelerators. Q is preferably halogen, alkoxy, aryloxy, alkyl- or arylthio, or a 5- or 6-membered, nitrogen-containing, heterocyclic group which is bonded to the coupling site via a nitrogen atom.

Pyrazolotetrazoles are described in JP-A-85/33 552; pyrazolopyrazoles in JP-A-85/43 695; pyrazoloimidazoles in JP-A-85/35 732, JP-A-86/18 949 and U.S. Pat. No. 4,500,630; pyrazololtriazoles in JP-A-85/186 567, JP-A-86/47 557, JP-A-85/215 687, JP-A-85/197 688, JP-A-85/172 982, EP-A-119 860, EP-A-173 256, EP-A-178 789, EP-A-178 788 and in Research Disclosure 84/24 624.

Further pyrazoloazole magenta couplers are described in: JP-A-86/28 947, JP-A-85/140 241, JP-A-85/262 160, JP-A-85/213 937, JP-A-87/278 552, JP-A-87/279 340, JP-A-88/100 457, EP-A-177 765, EP-A-176 804, EP-A-170 164, EP-A-164 130, EP-A-178 794, DE-A-3 516 996, DE-A-3 508 766 and Research Disclosure 81/20 919, 84/24 531 and 85/25 758.

Examples of suitable couplers of this type are:

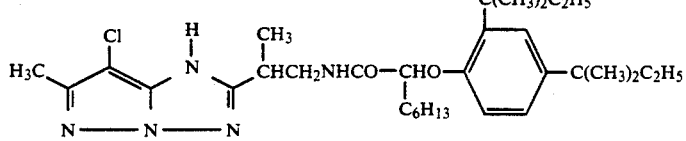

(M-5)

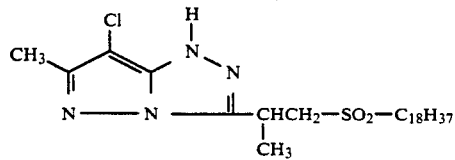
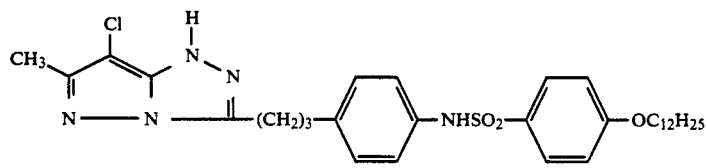
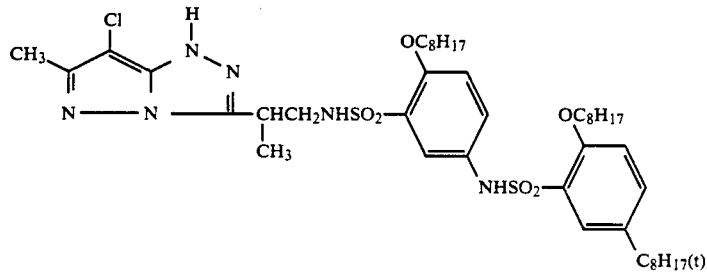
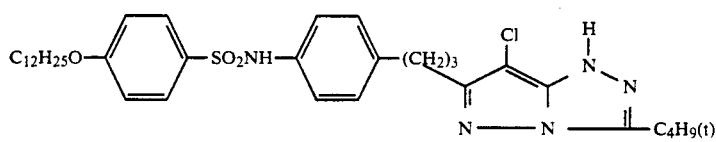
(M-6)
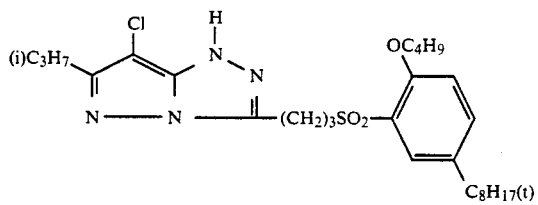
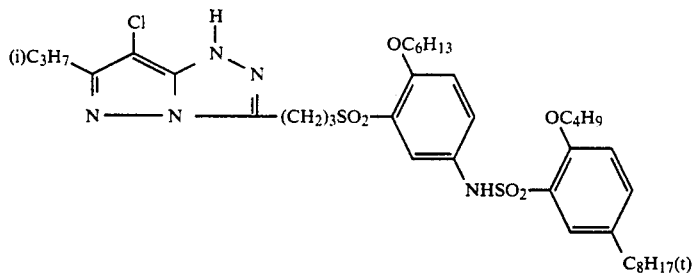
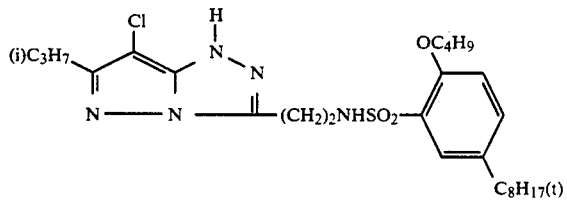
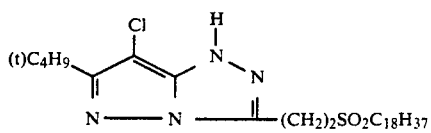

-continued
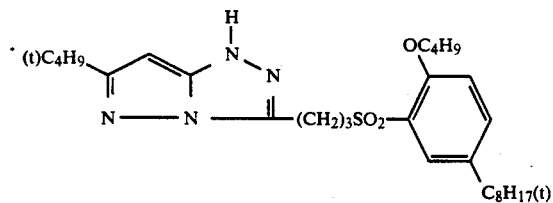
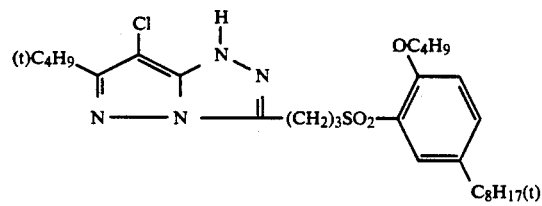
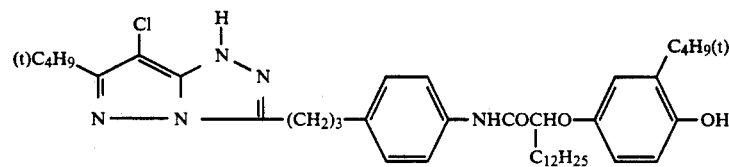
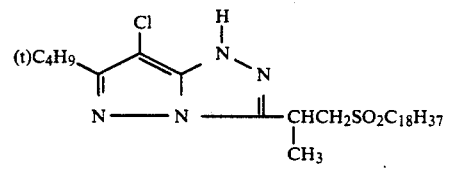
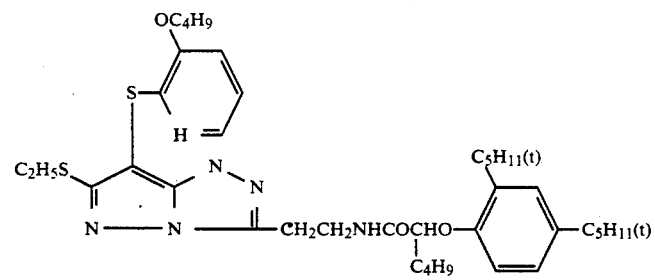
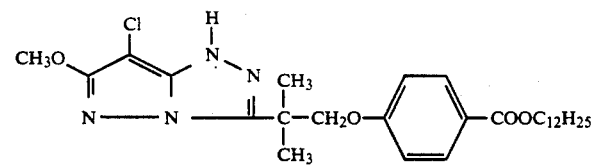
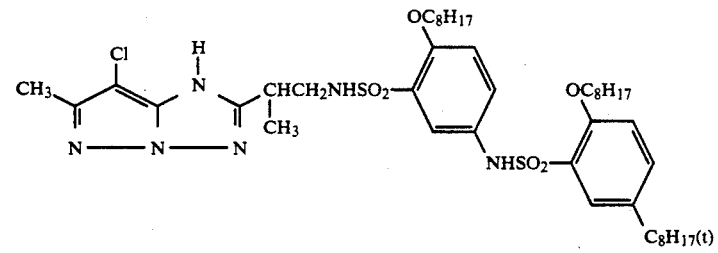
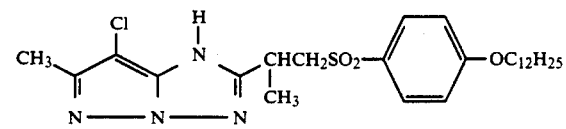

-continued
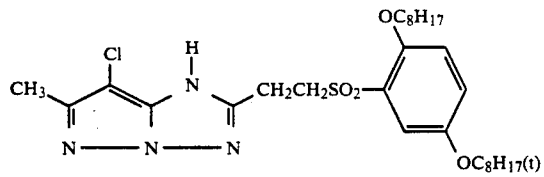
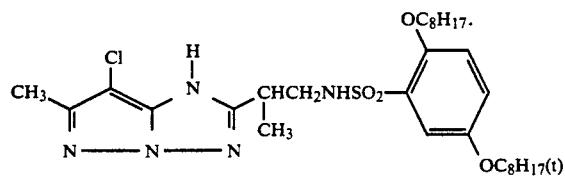
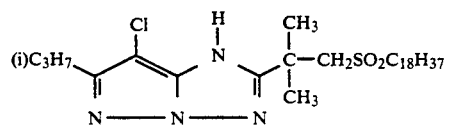
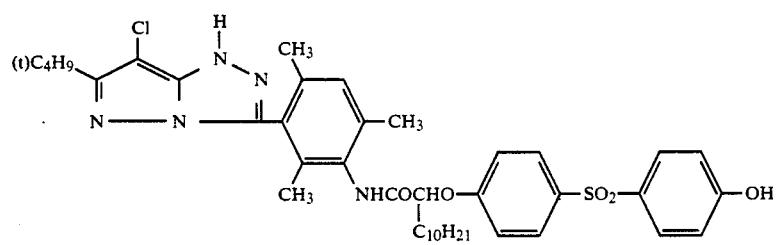
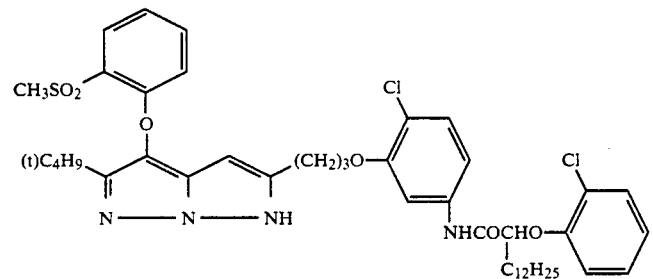
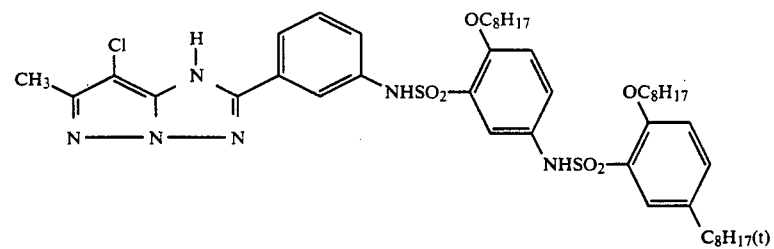
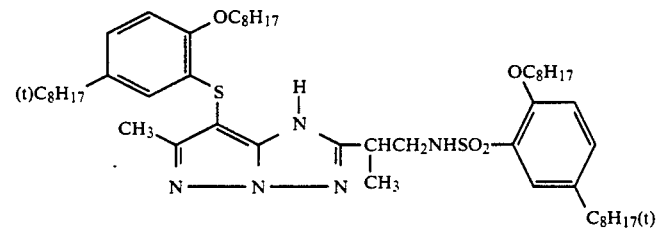

-continued
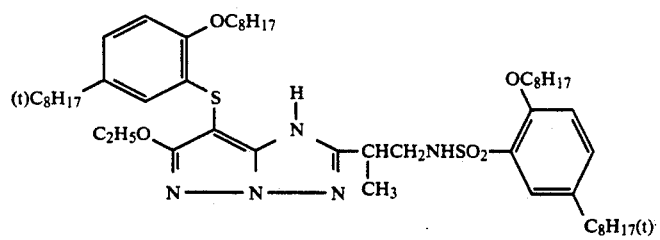
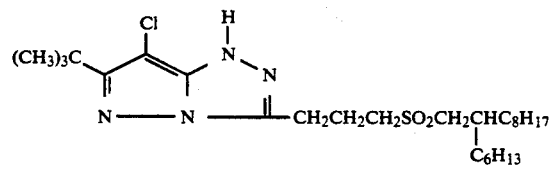
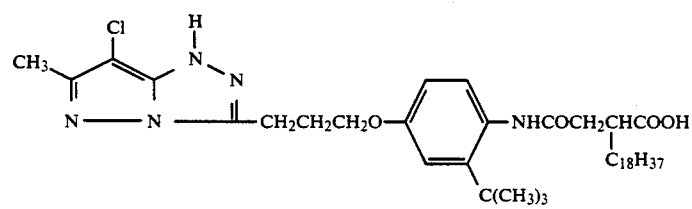
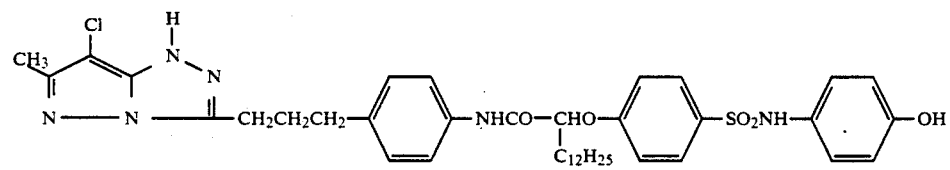
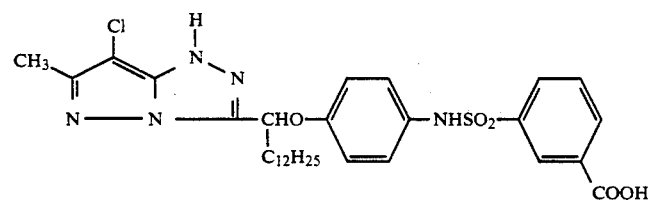
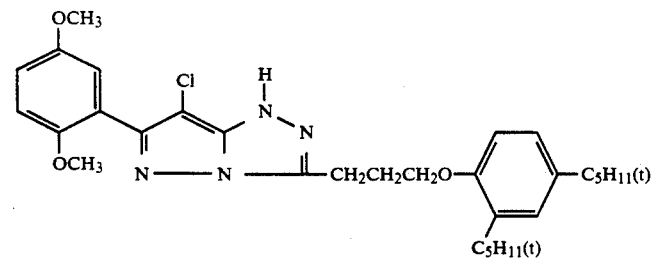
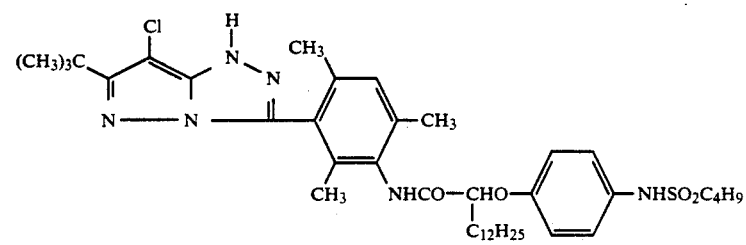

-continued
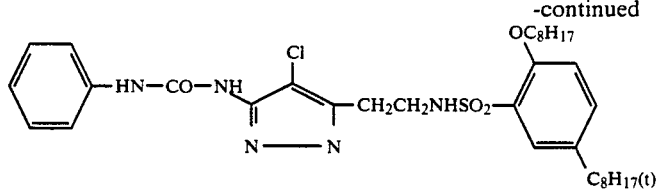
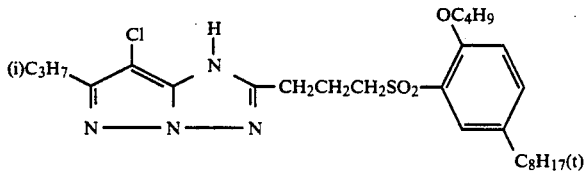
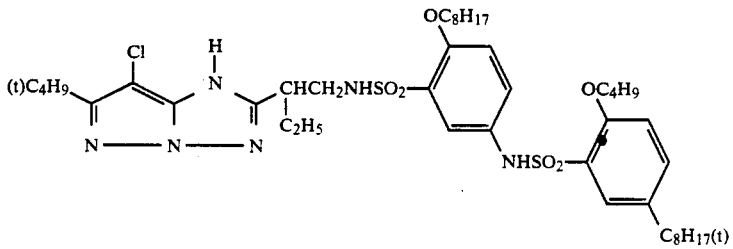
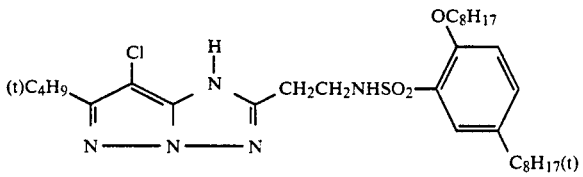
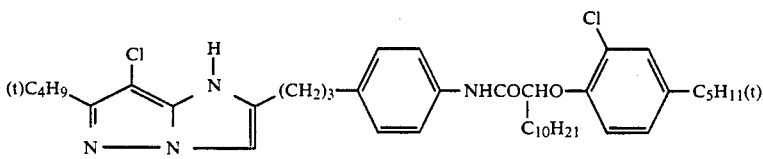
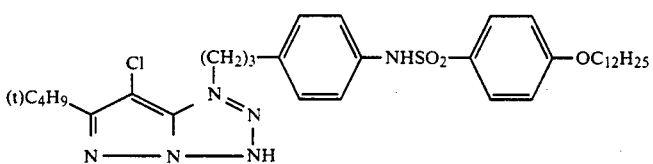
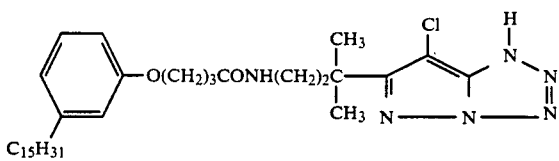
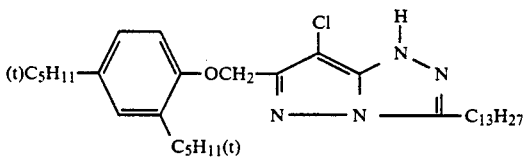
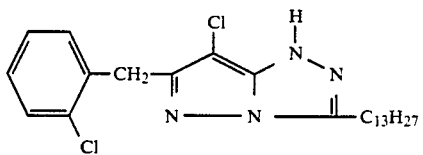

-continued
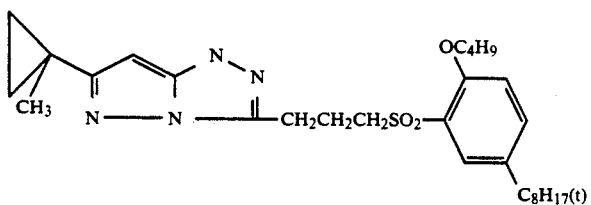
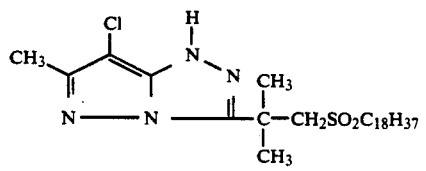
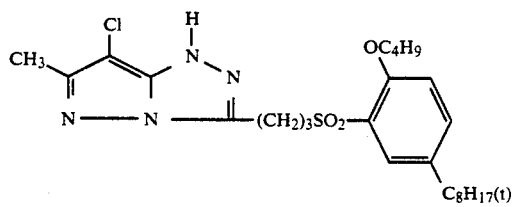
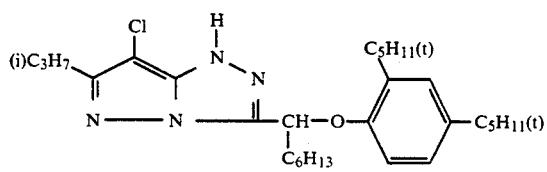
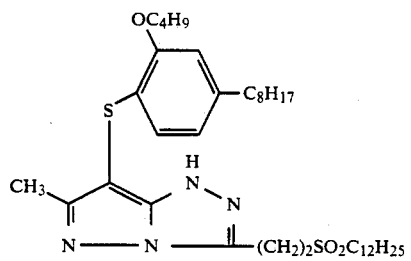
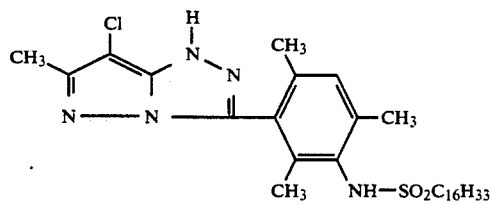
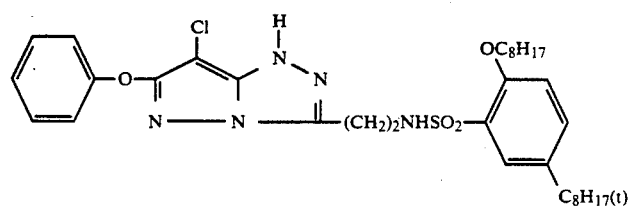

-continued
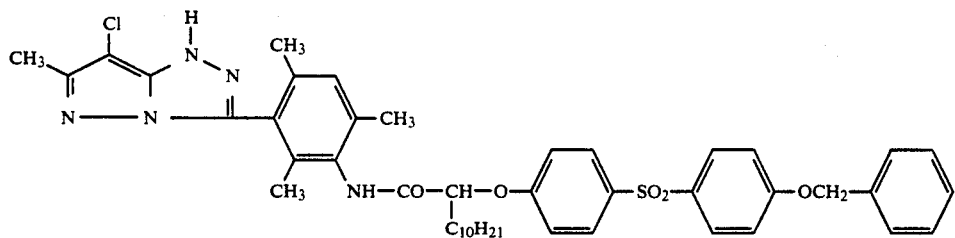
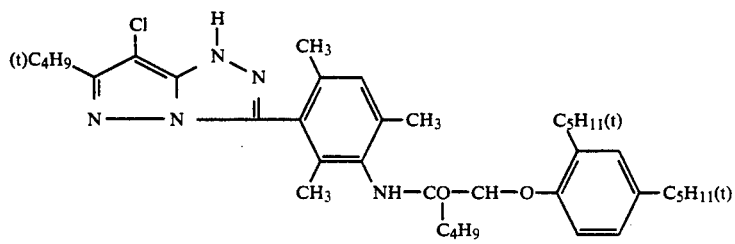
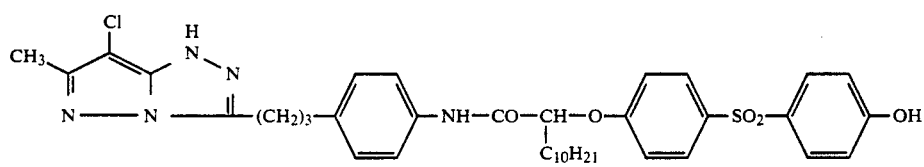
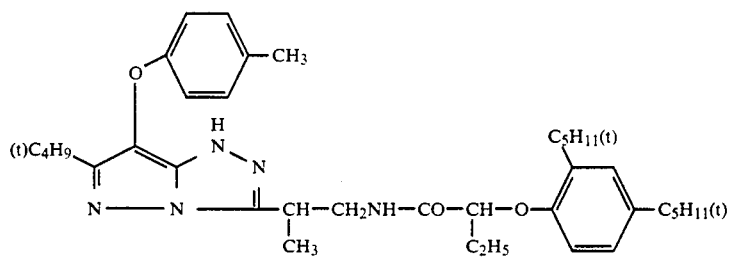
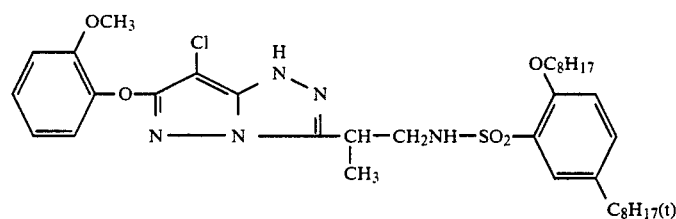
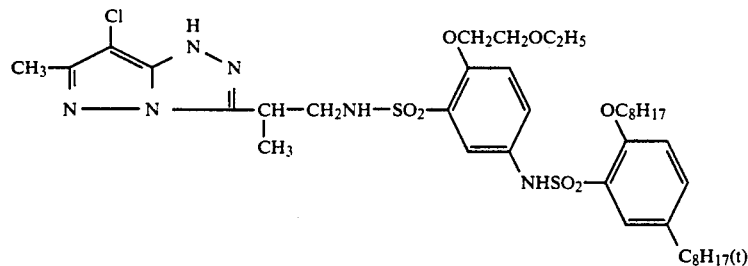
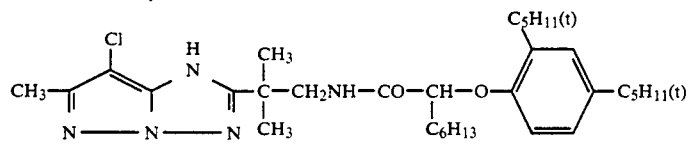

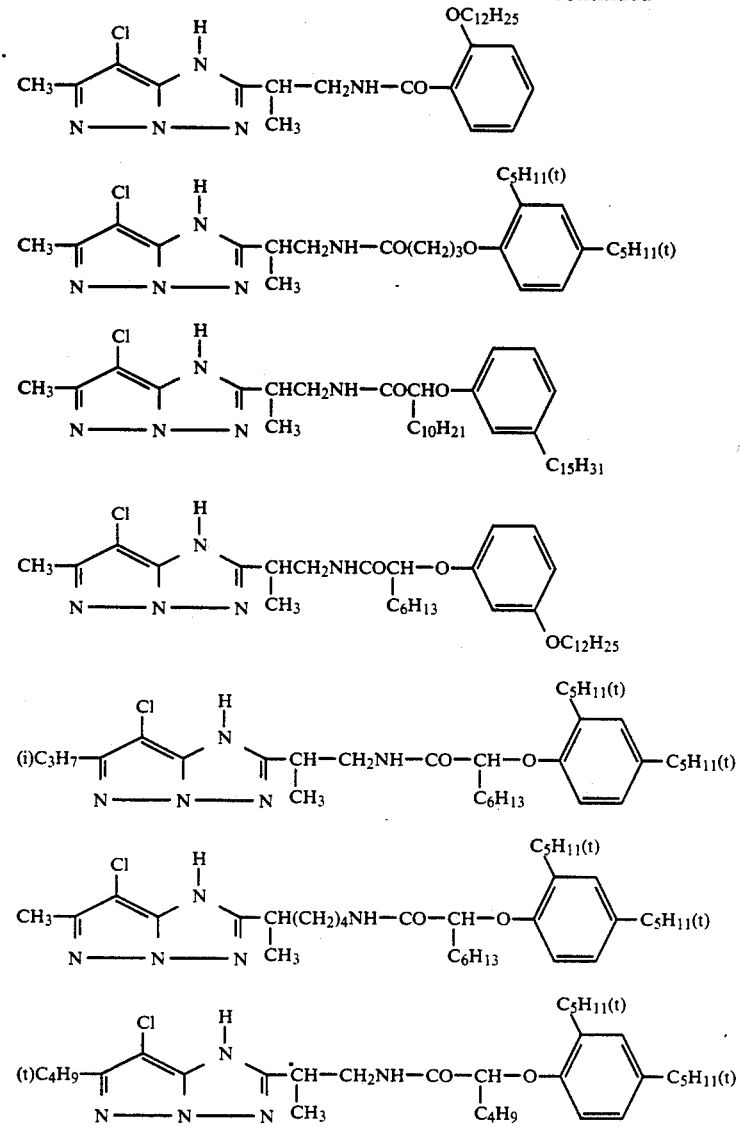

Cyan couplers may be, for example, derivatives of phenol, of 1-naphthol or to pyrazoloquinazolone. Preference is given to structures of the formula E

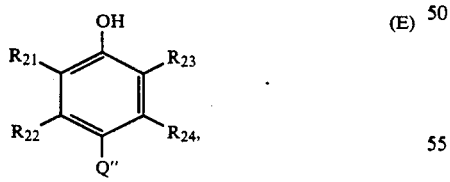

in which $R_{21}$, $R_{22}$, $R_{23}$ and $R_{24}$ are hydrogen, halogen, alkyl, carbamoyl, amino, sulfonamido, phosphoramido or ureido. $R_{21}$ is preferably H or Cl, $R_{22}$ is preferably an alkyl or amino group, $R_{23}$ is preferably an amino group and $R_{24}$ is preferably hydrogen. Q″ is hydrogen or a leaving group which can be eliminated during the reaction with the oxidised developer. A detailed list of cyan couplers is given in U.S. Pat. No. 4,456,681.

Examples of customary cyan couplers are the following:

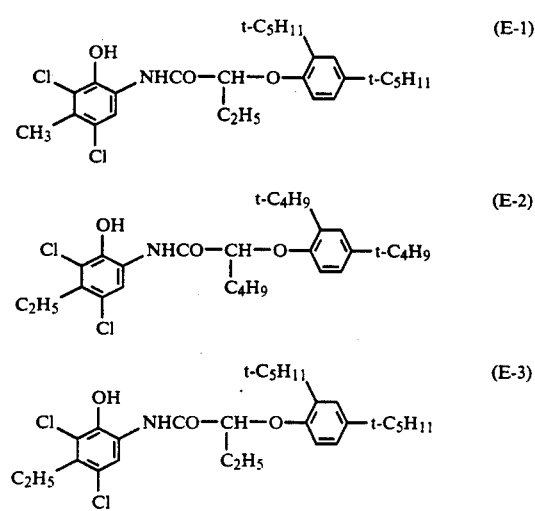

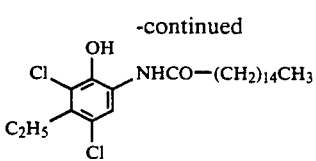

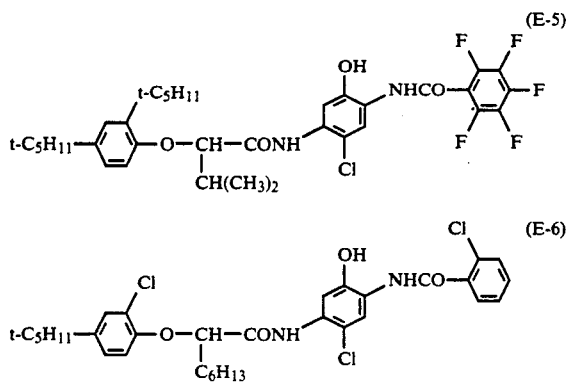

Further examples of cyan couplers are given in the following: U.S. Pat. Nos. 2,369,929, 2,423,730, 2,434,272, 2,474,293, 2,521,293, 2,521,908, 2,698,794, 2,706,684, 2,772,162, 2,801,171, 2,895,826, 2,908,573, 3,034,892, 3,046,129, 3,227,550, 3,253,294, 3,311,476, 3,386,301, 3,419,390, 3,458,315, 3,476,560, 3,476,563, 3,516,831, 3,560,212, 3,582,322, 3,583,971, 3,591,383, 3,619,196, 3,632,347, 3,652,286, 3,737,326, 3,758,308, 3,839,044, 3,880,661, 4,004,929, 4,124,396, 4,333,999, 4,463,086, 4,456,681, 4,873,183 and 4,923,791 and in EP-A-354 549 and EP-A-398 664.

The red-sensitive silver-halide emulsion layer of the material according to the invention preferably contains a cyan coupler of the formula

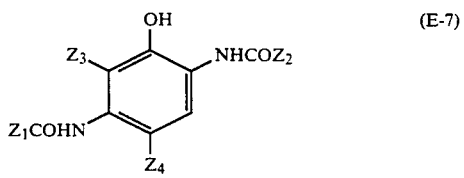

and/or of the formula

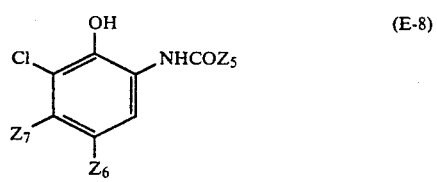

in which $Z_1$ is alkyl or aryl, $Z_2$ is alkyl, cycloalkyl, aryl, a heterocyclic group or a ballast group, $Z_3$ is hydrogen or halogen, $Z_1$ and $Z_3$ together can form a ring, and $Z_4$ is hydrogen or a leaving group, and $Z_5$ is a ballast group, $Z_6$ is hydrogen or a leaving group and $Z_7$ is alkyl.

The colour developers usually used for colour-photographic materials are p-dialkylaminoanilines. Examples of these are 4-amino-N,N-diethylaniline, 3-methyl-4-amino-N,N-diethylaniline, 4-amino-N-ethyl-N-α-hydroxyethylaniline, 3-methyl-4-amino-N-ethyl-N-α-hydroxyethylaniline, 3-methyl-4-amino-N-ethyl-N-α-hydroxyethylaniline, 3-methyl-4-amino-N-ethyl-N-α-methanesulphonamidoethylaniline, 3-methyl-4-amino-N-ethyl-N-α-methoxyethyl-aniline, 3-α-methanesulphonamidoethyl-4-amino-N,N-diethylaniline, 3-methoxy-4-amino-N-ethyl-N-α-hydroxyethylaniline, 3-methoxy-4-amino-N-ethyl-N-α-methoxyethylaniline, 3-acetamido-4-amino-N,N-diethylaniline, 4-amino-N,N-dimethylaniline, N-ethyl-N-α-[α'-(α''-methoxyethoxy)ethoxy]ethyl-3-methyl-4-aminoaniline, N-ethyl-N-α-(α'-methoxyethoxy)ethyl-3-methyl-4-aminoaniline, and the salts of these compounds, for example sulfates, hydrochlorides or toluene-sulfonates.

The UV absorbers of the formulae (I) and (III) used according to the invention can be incorporated into the colour-photographic material alone or together with the colour coupler and if desired further additives by predissolving them in high-boiling organic solvents. Preference is given to solvents which boil higher than 160° C. Typical examples of these solvents are the esters of phthalic acid, phosphoric acid, citric acid, benzoic acid or fatty acids, and alkylamides and phenols.

A low-boiling solvent is usually used in addition in order to simplify incorporation of the additives into the colour-photographic material. Examples of such solvents are esters, for example ethyl acetate, alcohols, for example butanol, ketones, for example methyl isobutyl ketone, chlorinated hydrocarbons, for example methylene chloride, and amides, for example dimethylformamide. If the additives are themselves liquid, they can also be incorporated into the photographic material without the assistance of solvents.

The UV absorbers according to this invention may also be dispersed without oil in the gelatine layer; Research Disclosure 88/296017 and 89/303070.

Further details on high-boiling solvents which can be used are given in the publications below:

Phosphates: GB-A-791 219, BE-A-755 248, JP-A-76/76 739, 78/27 449, 78/218 252, 78/97 573, 79/148 133, 82/216 177, 82/93 323 and 83/216 177 and EP-A-265 296.

Phthalates: GB-A-791 219, JP-A-77/98 050, 82/93 322, 82/216 176, 82/218 251, 83/24 321, 83/45 699 and 84/79 888.

Amides: GB-A-791 129, JP-A-76/105 043, 77/13 600, 77/61 089, 84/189 556, 87/239 149, U.S. Pat. No. 928,741, EP-A-270 341 and WO 88/00 723.

Phenols: GB-A-820 329, FR-A-1 220 657, JP-A-69/69 946, 70/3 818, 75/123 026, 75/82 078, 78/17 914, 78/21 166, 82/212 114 and 83/45 699.

Other oxygen-containing compounds: U.S. Pat. Nos. 3,748,141, 3,779,765, JP-A-73/75 126, 74/101 114, 74/10 115, 75/101 625, 76/76 740, 77/61 089, EP-A-304 810 and BE-A-826 039.

Other compounds: JP-A-72/115 369, 72/130 258, 73/127 521, 73/76 592, 77/13 193, 77/36 294, 79/95 233, 91/2 748, 83/105 147 and Research Disclosure 82/21 918.

The amount of high-boiling solvent is, for example, in the range from 50 mg to 2 g per m² of base, preferably from 200 mg to 1 g per m².

The photographic layers may furthermore contain colour cast inhibitors. These prevent colour casts being formed, due, for example, to reaction of the coupler with unintensionally oxidised developer or with by-products of the colour-formation process. Colour cast inhibitors of this type are usually hydroquinine derivatives, but may also be derivatives of aminophenols, of gallic acid or of ascorbic acid. Typical examples of these inhibitors are given in the publications below:

U.S. Pat. Nos. 2,360,290, 2,336,327, 2,403,721, 2,418,613, 2,675,314, 2,701,197, 2,704,713, 2,728,659, 2,732,300, 2,735,365; EP-A-124 877, EP-A-277 589, EP-A-338 785; JP-A-75/92 988, 75/92 989, 75/93 928, 75/110 337, 84/5 247 and 77/146 235.

Photographic layers may also contain DIR couplers (DIR denotes Development Inhibition Release), which form colourless compounds with the oxidised developer. They are added to improve the sharpness and grain of the colour prints.

The photographic layers in the material according to the invention may also contain further UV absorbers. Examples of such UV absorbers are benzotriazoles, 2-hydroxybenzophenones, salicycic acid esters, acrylonitrile derivatives or thiazolines. Such UV absorbers are described in greater detail, for example, in the publications below: U.S. Pat. Nos. 3,314,794, 3,352,681, 3,705,805, 3,707,375, 4,045,229, 3,700,455, 3,533,794, 3,698,907, 3,705,805, 3,738,837, 3,762,272, 4,163,671, 4,195,999, 4,309,500, 4,431,726, 4,443,543, 4,576,908, 4,749,643, GB-A-1 564 089, EP-A-190 003 and JP-A-71/2 784, 81/111 826, 81/27 146, 88/53 543 and 88/55 542. Preferred UV absorbers are benzotriazoles, in particular 2-(2-hydroxyphenyl)benzotriazoles and preferably those of the above formula (III).

The photographic layers may also contain phenolic compounds which act as light stabilisers for the colour image and as colour cast inhibitors. They may be present in a light-sensitive layer (colour layer) or in an intermediate layer, alone or together with other additives. Such compounds are described in greater detail, for example, in the publications below: U.S. Pat. Nos. 3,700,455, 3,591,381, 3,573,052, 4,030,931, 4,174,220, 4,178,184, 4,228,235, 4,279,990, 4,346,165, 4,366,266, 4,447,523, 4,528,264, 4,581,326, 4,562,146, 4,559,297, GB-A-1 309 277, 1 547 302, 2 023 862, 2 135 788, 2 139 370, 2 156 091; DE-A-2 301 060, 2 347 708, 2 526 468, 2 621 203, 3 323 448; DD-A-200 691, 214 468; EP-A-106 799, 113 124, 125 522, 159 912, 161 577, 164 030, 167 762, 176 845, 246 766, 320 776; JP-A-74/134 326, 76/127 730, 76/30 462, 77/3 822, 77/154 632, 78/10 842, 79/48 535, 79/70 830, 79/73 032, 79/147 038, 79/154 325, 79/155 836, 82/142 638, 83/244 353, 84/5 246, 84/72 443, 84/87 456, 84/192 246, 84/192 247, 84/204 039, 84/204 040, 84/212 837, 84/220 733, 84/222 836, 84/228 249, 86/2 540, 86/8 843, 86/18 835, 86/18 836, 87/11 456, 87/42 245, 87/62 157, 86/6 652, 89/137 258 and in Research Disclosure 79/17 804.

The photographic layers may also contain certain phosphorus(III) compounds, in particular phosphites and phosphonites. These act as light stabilisers for the colour images and as dark-storage stabilisers for magenta couplers. They are preferably added to the high-boiling solvents together with the coupler. Phosphorus-(III) compounds of this type are described in greater detail, for example, in the publications below: U.S. Pat. Nos. 4,407,935, 4,436,811, 4,956,406, EP-A-181 289, JP-A-73/32 728, JP-A-76/1 420 and JP-A-55/66 741.

The photographic layers may also contain organometallic complexes which are light stabilisers for the colour images, in particular for the magenta dyes. Such compounds and combinations thereof with other additives are described in greater detail, for example, in the publications below: U.S. Pat. Nos. 4,050,938, 4,239,843, 4,241,154, 4,242,429, 4,241,155, 4,242,430, 4,273,854, 4,246,329, 4,271,253, 4,242,431, 4,248,949, 4,245,195, 4,268,605, 4,246,330, 4,269,926, 4,245,018, 4,301,223, 4,343,886, 4,346,165, 4,590,153; JP-A-81/167 138, 81/168 652, 82/30 834, 82/161 744; EP-A-137 271, 161 577, 185 506; DE-A-2 853 865.

The photographic layers may also contain hydroquinone compounds. These act as light stabilisers for the colour couplers and for the colour images and as scavengers of oxidised developer in the intermediate layers. They are used in particular in the magenta layer. Hydroquinone compounds of this type and combinations thereof with other additives are described in greater detail, for example, in the publications below: U.S. Pat. Nos. 2,360,290, 2,336,327, 2,403,721, 2,418,613, 2,675,314, 2,701,197, 2,710,801, 2,732,300, 2,728,659, 2,735,765, 2,704,713, 2,937,086, 2,816,028, 3,582,333, 3,637,393, 3,700,453, 3,960,570, 3,935,016, 3,930,866, 4,065,435, 3,982,944, 4,232,114, 4,121,939, 4,175,968, 4,179,293, 3,591,381, 3,573,052, 4,279,990, 4,429,031, 4,346,165, 4,360,589, 4,346,167, 4,385,111, 416,978, 4,430,425, 4,277,558, 4,489,155, 4,504,572, 4,559,297, FR-A-885 982; GB-A-891 158, 1 156 167, 1 363 921, 2 022 274, 2 066 975, 2 071 348, 2 081 463, 2 117 526, 2 156 091; DE-A-2 408 168, 2 726 283, 2 639 930, 2 901 520, 3 308 766, 3 320 483, 3 323 699; DD-A-216 476, 214 468, 214 469,EP-A-84 290, 110 214, 115 305, 124 915, 124 877, 144 288, 147 747, 178 165, 161 577; JP-A-75/33 733, 75/21 249, 77/128 130, 77/146 234, 79/70 036, 79/133 131, 81/83 742, 81/87 040, 81/109 345, 83/134 628, 82/22 237, 82/112 749, 83/17 431, 83/21 249, 84/75 249, 84/149 348, 84/182 785, 84/180 557, 84/189 342, 84/228 249, 84/101 650, 79/24 019, 79/25 823, 86/48 856, 86/48 857, 86/27 539, 86/6 652, 86/72 040, 87/11 455, 87/62 157, and in Research Disclosure 79/17 901, 79/17 905, 79/18 813,83/22 827 and 84/24 014.

The photographic layers may also contain derivatives of hydroquinone ethers. These compounds act as light stabilisers and are particularly suitable for stabilising magenta dyes. Such compounds and combinations thereof with other additives are described in greater detail, for example, in the publications below: U.S. Pat. Nos. 3,285,937, 3,432,300, 3,519,429, 3,476,772, 3,591,381, 3,573,052, 3,574,627, 3,573,050, 3,698,909, 3,764,337, 3,930,866, 4,113,488, 4,015,990, 4,113,495, 4,120,723, 4,155,765, 4,159,910, 4,178,184, 4,138,259, 4,174,220, 4,148,656, 4,207,111, 4,254,216, 4,134,011, 4,273,864, 4,264,720, 4,279,990, 4,332,886, 4,436,165, 4,360,589, 4,416,978, 4,385,111, 4,459,015, 4,559,297; GB-A 1 347 556, 1 366 441, 1 547 392, 1 557 237, 2 135 788; DE-A 3 214 567; DD-214 469, EP-A 161 577, 167 762, 164 130, 176 845; JP-A 76/123 642, 77/35 633, 77/147 433, 78/126, 78/10 430, 78/53 321, 79/24 019, 79/25 823, 79/48 537, 79/44 521, 79/56 833, 79/70 036, 79/70 830, 79/73 032, 79/95 233, 79/145 530, 80/21 004, 80/50 244, 80/52 057, 80/70 840, 80/139 383, 81/30 125, 81/151 936, 82/34 552, 82/68 833, 82/ 204 306 82/204 037, 83/134 634, 83/207 039, 84/60 434, 84/101 650, 84/87 450, 84/149 348, 84/182 785, 86/72 040, 87/11 455, 87/62 157, 87/63 149, 86/2 151, 86/6 652, 86/48 855, 89/309 058 and in Research Disclosure 78/17 051.

Examples of suitable stabilisers for the magenta couplers are:

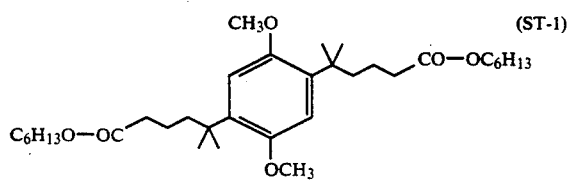
(ST-1)

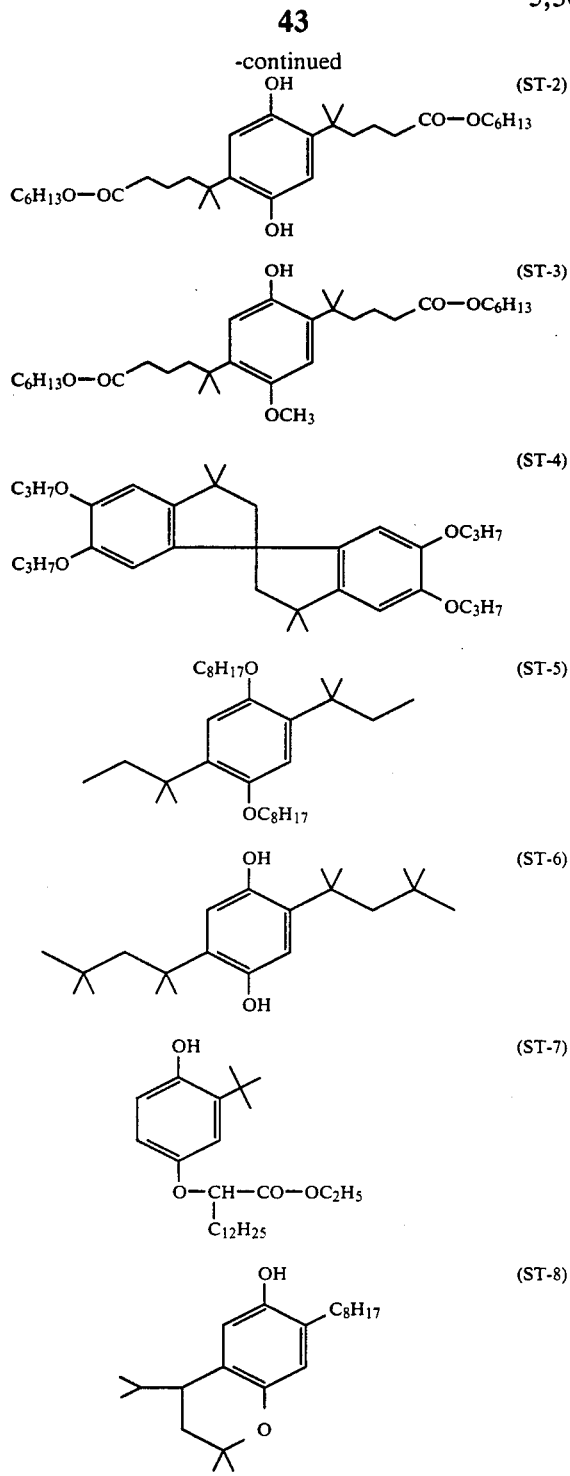

tion. The same applies to the bases mentioned in the publication.

The silver-halide emulsion which can be used for carrying out this invention can be sensitised for all desired wavelengths with the aid of sensitisation pigments. For this purpose, it is possible to use cyanine pigments, merocyanine pigments, holopolar pigments, hemicyanine pigments, styryl pigments or hemioxanol pigments.

The photosensitive material may contain water-soluble dyes in order, for example, to improve the clarity by preventing radiation damage. For this purpose, it is possible to use oxanol dyes, hemioxanol dyes, styryl dyes, merocyanine dyes, cyanine dyes, anthraquinone dyes and azo dyes.

It is also possible to use further materials, as described, for example, in JP-A-87/215 272, 92/9 035 and 92/21 840 and EP-A-429 240, together with the material according to the invention.

The present invention also relates to compounds of the formula

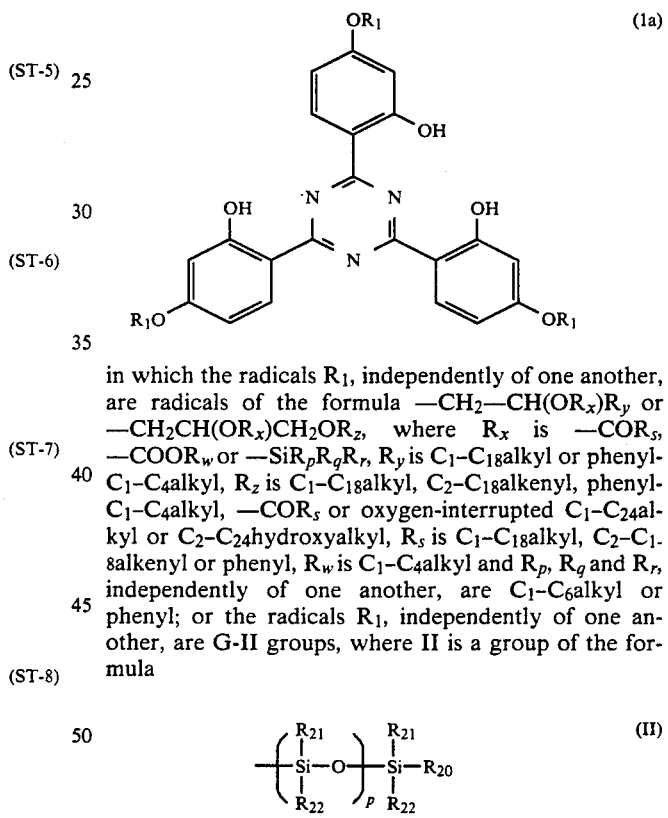

in which the radicals $R_1$, independently of one another, are radicals of the formula $-CH_2-CH(OR_x)R_y$ or $-CH_2CH(OR_x)CH_2OR_z$, where $R_x$ is $-COR_s$, $-COOR_w$ or $-SiR_pR_qR_r$, $R_y$ is $C_1-C_{18}$alkyl or phenyl-$C_1-C_4$alkyl, $R_z$ is $C_1-C_{18}$alkyl, $C_2-C_{18}$alkenyl, phenyl-$C_1-C_4$alkyl, $-COR_s$ or oxygen-interrupted $C_1-C_{24}$alkyl or $C_2-C_{24}$hydroxyalkyl, $R_s$ is $C_1-C_{18}$alkyl, $C_2-C_{18}$alkenyl or phenyl, $R_w$ is $C_1-C_4$alkyl and $R_p$, $R_q$ and $R_r$, independently of one another, are $C_1-C_6$alkyl or phenyl; or the radicals $R_1$, independently of one another, are G-II groups, where II is a group of the formula $$\left(\begin{array}{c}R_{21}\\|\\-Si-O\\|\\R_{22}\end{array}\right)_p\begin{array}{c}R_{21}\\|\\-Si-R_{20}\\|\\R_{22}\end{array}\quad(II)$$

and G is a direct bond or a divalent group of one of the following formulae:

$-(CH_2)_q-$, $-(CH_2)_q-O-$, $-(CH_2)_q-O-R_{26}-$, $-(CH_2)_q-CO-X-(CH_2)_r-$, $-(CH_2)_q-CO-X-(CH_2)_r-O-$,

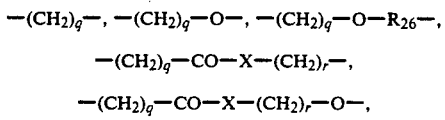,

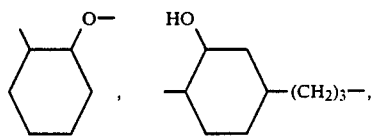

Silver-halide emulsions which can be used are conventional silver chloride, silver bromide or silver iodide emulsions or mixtures thereof, such as silver chlorobromide and silver chloroiodide emulsions, in which the silver halides may have any known crystal form. The use of silver-chloride emulsions is particularly important in the material according to the invention. The preparation of such emulsions and the sensitisation thereof are described in RESEARCH DISCLOSURE, Nov. 1989, No. 307 105. This publication furthermore mentions a number of binders for said emulsions which can also be used in the materials according to the inven- -continued

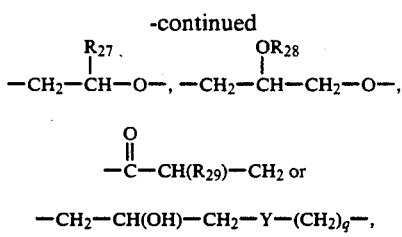

$$-CH_2-CH(R_{29})-CH_2 \text{ or}$$

$$-CH_2-CH(OH)-CH_2-Y-(CH_2)_q-,$$

in which q and r, independently of one another, are 1–4 and p is 0–50, $R_{26}$ is $C_1-C_{12}$alkylene, cyclohexylene or phenylene, $R_{27}$ is $C_1-C_{12}$alkyl, $C_5-C_8$cycloalkyl, phenyl, $C_2-C_{13}$alkoxymethyl, $C_6-C_9$cycloalkoxymethyl or phenoxymethyl, $R_{28}$ is a group of the formula G-II, $R_{29}$ is hydrogen or methyl, X is —O— or —NR$_{23}$—, in which $R_{23}$ is hydrogen, $C_1-C_{12}$alkyl or a —(CH$_2$)$_3$—G-II or —(CH$_2$)$_3$—O—G-II group, Y is —O— or —NH—, and $R_{20}$, $R_{21}$ and $R_{22}$, independently of one another, are $C_1-C_{18}$alkyl, cyclohexyl, phenyl or $C_1-C_{18}$alkoxy.

Especially preferred compounds are those mentioned in the description of the photographic material.

The examples below illustrate the invention in greater detail.

EXAMPLE 1

A polyethylene-coated base material is first coated with a gelatine layer comprising silver bromide, a magenta coupler and a stabiliser, and then with a gelatine layer containing the UV absorber of the formula (1) (top layer).

The gelatine layers comprise the following components (per m² of base material):

| Component | AgBr layer | Top layer |
|---|---|---|
| Gelatine | 5.15 g | 1.2 g |
| Curing agent | 300 mg | 40 mg |
| Wetting agent | 85 mg | 100 mg |
| Silver bromide | 520 mg* | — |
|  | 260 mg** | — |
| Isononyl phosphate | A | 510 mg |
| Magenta coupler | 0.535 mM | — |
| UV absorber | — | 300 mg |
| Stabiliser | B | — |

*when tetraequivalent couplers are used
**when diequivalent couplers are used
A (amount of oil) = 50% of the amount of magenta coupler
B (amount of stabiliser) = 35% of the amount of magenta coupler The curing agent used is 2,4-dichloro-6-hydroxytriazine, and the wetting agent used is the sodium salt of diisobutylnaphthalenesulfonic acid.

The amounts of magenta coupler and stabiliser are shown in Table 2.

A step wedge having a density difference of 0.15 logE per step is exposed onto each of the samples obtained in this way, and the samples are subsequently processed in accordance with the manufacturer's instructions by the Kodak E+2 process for colour negative paper.

After exposure and processing, the remission density in green for the magenta step is measured at a density between 0.9 and 1.1 of the wedge. The wedge is then exposed in an Atlas exposure unit with a total of 45 kJ/cm² and the remission density is remeasured.

The loss of dye ($-\Delta D$) is shown in Table 2 in %.

TABLE 2

| Sample No. | Magenta coupler (mg) | Stabiliser (mg) | UV absorber No. | $-\Delta D$ |
|---|---|---|---|---|
| 1 | M-1 (329) | ST-4 (118) | (3) | 35 |
| 2 | M-2 (417) | ST-8 (144) | (3) | 29 |
| 3 | M-2 (417) | ST-8 (144) | (14) | 28 |
| 4 | M-3 (394) | ST-5 (128) | (3) | 29 |
| 5 | M-3 (394) | ST-5 (128) | (14) | 28 |
| 6 | M-4 (485) | ST-1 (171) | (3) | 22 |
| 7 | M-4 (485) | ST-1 (171) | (14) | 19 |
| 8 | M-4 (485) | ST-2 (171) | (3) | 29 |
| 9 | M-4 (485) | ST-2 (175) | (14) | 28 |
| 10 | M-4 (485) | ST-4 (171) | (3) | 20 |
| 11 | M-4 (485) | ST-4 (171) | (14) | 18 |
| 12 | M-1 (329) | ST-7 (118) | (3) | 39 |
| 13 | M-1 (329) | ST-7 (118) | (14) | 40 |
| 14 | M-1 (329) | ST-6 (118) | (3) | 65 |
| 15 | M-1 (329) | ST-6 (118) | (14) | 65 |
| 16 | M-5 (306) | ST-4 (107) | (3) | 15 |
| 17 | M-5 (306) | ST-4 (107) | (14) | 16 |
| 18 | M-5 (306) | ST-4 (107) | (15) | 15 |
| 19 | M-5 (306) | ST-1 (107) | (3) | 17 |
| 20 | M-5 (306) | ST-1 (107) | (14) | 17 |
| 21 | M-1 (329) | ST-4 (118) | (14) | 36 |
| 22 | M-1 (329) | ST-4 (118) | (15) | 35 |
| 23 | M-1 (329) | ST-4 (118) | — | 47 |
| 24 | M-2 (417) | ST-8 (144) | — | 68 |
| 25 | M-3 (394) | ST-5 (128) | — | 56 |
| 26 | M-4 (485) | ST-1 (170) | — | 71 |
| 27 | M-4 (485) | ST-2 (171) | — | 59 |
| 28 | M-4 (485) | ST-4 (107) | — | 60 |
| 29 | M-1 (329) | ST-7 (118) | — | 55 |
| 30 | M-1 (329) | ST-6 (118) | — | 83 |
| 31 | M-5 (306) | ST-4 (107) | — | 34 |
| 32 | M-5 (306) | ST-1 (107) | — | 37 |

EXAMPLE 2

If Example 1 is repeated, but 150 mg of UV absorber and 150 mg of hydroxybenzotriazole are used, the values for the loss of dye ($-\Delta D$) in % shown in Table 3 are obtained.

TABLE 3

| Sample No. | Magenta coupler (mg) | Stabiliser (mg) | UV absorber No. | $-\Delta D$ |
|---|---|---|---|---|
| 33 | M-1 (329) | ST-4 (118) | — | 47 |
| 34 | M-1 (329) | ST-4 (118) | (3) HBT-1 | 38 |
| 35 | M-1 (329) | ST-4 (118) | (14) HBT-1 | 37 |
| 36 | M-5 (306) | ST-4 (118) | — | 34 |
| 37 | M-5 (306) | ST-4 (108) | (3) HBT-1 | 17 |
| 38 | M-5 (306) | ST-4 (118) | (14) HBT- | 18 |
| 39 | M-5 (306) | ST-4 (118) | (3) HBT-2 | 16 |
| 40 | M-5 (306) | ST-4 (118) | (14) HBT-2 | 16 |
| 41 | M-5 (306) | ST-1 (171) | — | 37 |
| 42 | M-5 (306) | ST-1 (171) | (3) HBT-1 | 19 |
| 43 | M-5 (306) | ST-1 (171) | (3) HBT-2 | 19 |

EXAMPLE 3

If Example 1 is repeated, but 150 mg of each of two UV absorbers are used, the values for the loss of dye ($-\Delta D$) in % shown in Table 4 are obtained.

TABLE 4

| Sample No. | Magenta coupler (mg) | Stabiliser (mg) | UV absorber No. | $-\Delta D$ |
|---|---|---|---|---|
| 44 | M-5 (306) | ST-4 (171) | — | 37 |
| 45 | M-5 (306) | ST-1 (171) | (3), (14) | 16 |

EXAMPLE 4

If Example 1 is repeated, but 100 mg of each of three UV absorbers are used, the values for the loss of dye ($-\Delta D$) in % shown in Table 5 are obtained.

TABLE 5

| Sample No. | Magenta coupler (mg) | Stabiliser (mg) | UV absorber No. | $-\Delta D$ |
|---|---|---|---|---|
| 46 | M-5 (306) | ST-4 (171) | — | 37 |
| 47 | M-5 (306) | ST-1 (171) | (3), (14), (15) | 17 |

The samples containing a UV absorber according to the invention showed a smaller decrease in the magenta density.

EXAMPLE 5

The procedure is as in Example 1, but with no stabiliser and using a cyan coupler. The composition of the gelatine layers (per m²) is as follows:

| Component | AgBr layer | Top layer |
|---|---|---|
| Gelatine | 5.15 g | 1.2 g |
| Curing agent | 300 mg | 40 mg |
| Wetting agent | 170 mg | 100 mg |
| Silver bromide | 260 mg | — |
| Tricresyl phosphate | A | 510 mg |
| Cyan coupler | 0.535 mM | — |
| UV absorber | — | 300 mg |

A (amount of oil) = 1.5 × amount of cyan coupler
The amounts of cyan coupler are shown in Table 6.

After exposure and processing as described in Example 1, the remission density in red for the cyan step is measured at a density between 0.9 and 1.1 of the wedge. The wedge is then exposed in an Atlas exposure unit with a total of 45 kJ/cm² and the remission density is remeasured. The loss of dye ($-\Delta D$) is shown in Table 6 in %.

TABLE 6

| Sample No. | Cyan coupler (mg) | UV absorber No. | $-\Delta D$ (%) |
|---|---|---|---|
| 48 | E-1 (264) | (3) | 16 |
| 49 | E-2 (272) | (3) | 23 |
| 50 | E-3 (272) | (3) | 22 |
| 51 | E-5 (358) | (3) | 31 |
| 52 | E-6 (331) | (3) | 32 |
| 53 | E-1 (264) | (14) | 16 |
| 54 | E-3 (272) | (14) | 21 |
| 55 | E-5 (358) | (14) | 30 |
| 56 | E-2 (272) | (14) | 23 |
| 57 | E-6 (331) | (14) | 33 |
| 58 | E-1 (264) | — | 28 |
| 59 | E-2 (272) | — | 31 |
| 60 | E-3 (272) | — | 28 |
| 61 | E-5 (358) | — | 54 |
| 62 | E-6 (331) | — | 50 |

The samples containing a UV absorber according to the invention showed a smaller decrease in the density of the cyan dye.

EXAMPLE 6

A polyethylene-coated base material is coated with a gelatine layer comprising silver bromide, a cyan coupler and a UV absorber of the formula (I).

The composition of the gelatine layer is as follows (per m² of base material):

| Component | AgBr Layer |
|---|---|
| Gelatine | 5.15 g |
| Curing agent | 300 mg |
| Wetting agent (anionic) | 170 mg |
| Silver bromide | 260 mg |
| Tricresyl phosphate | A |
| Cyan coupler | 0.535 mM |
| UV absorber | see Table Y |

A (amount of oil) = 1.5 × cyan coupler

After exposure and processing as described in Example 1, the remission density in red for the cyan step is measured at a density of between 0.9 and 1.1 of the wedge. The wedge is then exposed in an Atlas exposure unit with 30 kJ/cm², and the remission density is remeasured. The loss of dye ($-\Delta D$) is shown in Table 7 in %.

TABLE 7

| Sample No. | Cyan coupler (mg) | UV absorber No. | $-\Delta D$ (%) |
|---|---|---|---|
| 63 | E-5 (358) | — | 54 |
| 64 | E-5 (358) | (3) | 36 |
| 65 | E-5 (358) | (14) | 40 |
| 66 | E-6 (331) | — | 50 |
| 67 | E-6 (331) | (3) | 42 |
| 68 | E-6 (331) | (14) | 45 |

EXAMPLE 7

The procedure is as in Example 1, but with no stabiliser and using a yellow coupler.

The composition of the gelatine layers (per m²) is as follows:

| Component | AgBr layer | Top layer |
|---|---|---|
| Gelatine | 5.15 g | 1.2 g |
| Curing agent | 300 mg | 40 mg |
| Wetting agent (anionic) | 340 mg | 100 mg |
| Silver bromide | 520 mg | — |
| Tricresyl phosphate | A | 510 mg |
| Yellow coupler | 1.07 mM | — |
| UV absorber | — | 300 mg |

A (amount of oil) = 33% of the amount of yellow coupler

The amount of yellow coupler is shown in Table 4.

After exposure and processing as described in Example 1, the remission density in blue for the yellow step is measured at a density between 0.9 and 1.1 of the wedge. The wedge is then exposed in an Atlas exposure unit with a total of 30 kJ/cm² and the remission density is remeasured. The loss of dye (−ΔD) is shown in Table 8 in %.

TABLE 8

| Sample No. | Yellow coupler (mg) | UV absorber No. | −ΔD (%) |
|---|---|---|---|
| 69 | Y-1 (819) | (3) | 21 |
| 70 | Y-2 (859) | (3) | 14 |
| 71 | Y-3 (973) | (3) | 16 |
| 72 | Y-4 (812) | (3) | 22 |
| 73 | Y-6 (813) | (3) | 26 |
| 74 | Y-8 (927) | (3) | 24 |
| 75 | Y-1 (819) | (14) | 21 |
| 76 | Y-2 (859) | (14) | 14 |
| 77 | Y-3 (873) | (14) | 17 |
| 78 | Y-4 (812) | (4) | 27 |
| 79 | Y-6 (813) | (4) | 26 |
| 80 | Y-8 (927) | (14) | 25 |
| 81 | Y-8 (927) | (15) | 26 |
| 82 | Y-1 (819) | — | 46 |
| 83 | Y-2 (859) | — | 33 |
| 84 | Y-3 (973) | — | 50 |
| 85 | Y-4 (812) | — | 43 |
| 86 | Y-6 (813) | — | 48 |
| 87 | Y-8 (927) | — | 62 |

The samples containing a UV absorber according to the invention show a smaller decrease in the yellow dye density.

EXAMPLE 8

The procedure is as in Example 1.

The amounts of magenta coupler and stabiliser are shown in Table 9.

The remission density in blue for yellowing is measured. The wedge is then exposed in an Atlas exposure unit with a total of 30 kJ/cm², the remission density (in blue) is remeasured, and the increase in yellow dye ($-\Delta D_B$) is calculated. The yellowing is shown in Table 9.

TABLE 9

| Sample No. | Magenta coupler (mg) | Stabiliser (mg) | UV absorber No. | −ΔD (%) |
|---|---|---|---|---|
| 88 | M-1 (329) | ST-4 (118) | (3) | 3 |
| 89 | M-1 (329) | ST-4 (118) | (14) | 22 |
| 90 | M-1 (329) | ST-4 (118) | — | 38 |
| 91 | M-1 (329) | ST-7 (118) | (3) | 14 |
| 92 | M-1 (329) | ST-7 (118) | (14) | 14 |
| 93 | M-1 (329) | ST-7 (118) | — | 32 |
| 94 | M-1 (329) | ST-6 (118) | (3) | 10 |
| 95 | M-1 (329) | ST-6 (118) | — | 20 |
| 96 | M-2 (417) | ST-8 (144) | (3) | 18 |
| 97 | M-2 (417) | ST-8 (144) | — | 24 |
| 98 | M-3 (394) | ST-5 (128) | (3) | 13 |
| 99 | M-3 (394) | ST-5 (128) | (14) | 12 |
| 100 | M-3 (394) | ST-5 (128) | — | 25 |
| 101 | M-4 (485) | ST-1 (171) | (3) | 21 |
| 102 | M-4 (485) | ST-1 (171) | — | 29 |
| 103 | M-4 (485) | ST-2 (171) | (3) | 10 |
| 104 | M-5 (485) | ST-2 (171) | (14) | 11 |
| 105 | M-4 (485) | ST-2 (171) | — | 14 |
| 106 | M-4 (485) | ST-4 (107) | (3) | 22 |
| 107 | M-4 (485) | ST-4 (107) | — | 26 |

The samples containing a UV absorber according to the invention show less yellowing.

EXAMPLE 9

If Example 8 is repeated, but a stabilizer of the following formula

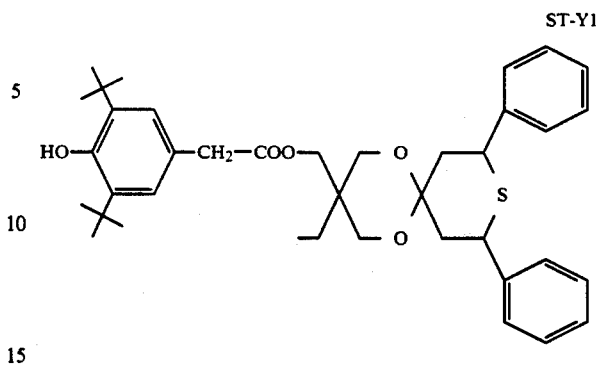

ST-Y1 is additionally added, the values for the loss of dye (−ΔD) in % shown in Table 10 are obtained.

TABLE 10

| Sample No. | Yellow coupler (mg) | Stabiliser (mg) | UV absorber No. | −ΔD (%) |
|---|---|---|---|---|
| 108 | Y-8 (927) | ST-Y1 (278) | — | 23 |
| 109 | Y-8 (927) | ST-Y1 (278) | (3) | 8 |
| 110 | Y-8 (927) | ST-Y1 (278) | (14) | 8 |
| 111 | Y-8 (927) | ST-Y1 (278) | (15) | 9 |

EXAMPLE 10

If Example 9 is repeated, but a UV absorber (150 mg) is used together with a hydroxybenzotriazole (150 mg), the values for the loss of dye (−ΔD) in % shown in Table 11 are obtained.

TABLE 11

| Sample No. | Yellow coupler (mg) | Stabiliser (mg) | UV absorber No. | −ΔD (%) |
|---|---|---|---|---|
| 112 | Y-8 (927) | ST-Y1 (278) | — | 23 |
| 113 | Y-8 (927) | ST-Y1 (278) | (3) | 8 |
| 114 | Y-8 (927) | ST-Y1 (278) | (3) / HBT-10 | 8 |
| 115 | Y-8 (927) | ST-Y1 (278) | (3) / HBT-5 | 9 |
| 116 | Y-8 (927) | ST-Y1 (278) | (3) / HBT-8 | 8 |

EXAMPLE 11

If Example 9 is repeated, but two UV abosrbers (150 mg each) are used, the values for the loss of dye (−ΔD) in % shown in Table 12 are obtained.

TABLE 12

| Sample No. | Yellow coupler (mg) | Stabiliser (mg) | UV absorber No. | −ΔD (%) |
|---|---|---|---|---|
| 117 | Y-8 (927) | ST-Y1 (278) | — | 23 |
| 118 | Y-8 (927) | ST-Y4 (278) | (3) / (14) | 8 |

EXAMPLE 12

The amount of UV absorber shown in the table below is dissolved in 2 ml of ethyl acetate. 1 ml of this solution is mixed with 9 ml of an aqueous gelatine solution (comprising 27.6 g/l of gelatine and 6.8 g/l of an 8% aqueous solution of 4,8-diisobutylnaphthalene-2-sulfonic acid (sodium salt) as wetting agent). This mixture is emulsified for 3 minutes by means of ultrasound. 7.5 ml of this UV absorber emulsion are mixed with 4.5 ml of an aqueous curing agent solution (comprising 0.24% of 2-hydroxy-4,6-dichloro-1,3,5-triazine, potassium salt). 8 ml of this emulsion are poured onto a polyester base (13×18 cm). The casting is cured for 7 days at room temperature. A UV spectrometer is then used to determine the values for the maximum density in the range from 330–380 nm. The sample is then exposed in an Atlas exposure unit with a total of 60 kJ/cm$^2$, the maximum density is remeasured, and the difference (−DD in %) between the corresponding values is calculated:

TABLE 13

| Sample No. | UV absorber (mg) | Loss of UV absorber −DD (%) Atlas 60 kJ/cm$^2$ |
|---|---|---|
| 119 | (3) (27) | 1 |
| 120 | (4) (33) | 0 |
| 121 | (5) (25) | 1 |
| 122 | (12) (25) | 0 |
| 123 | (7) (34) | 4 |
| 124 | (6) (21) | 2 |
| 125 | (14) (21) | 3 |
| 126 | (15) (21) | 3 |
| 127 | (16) (21) | 3 |
| 128 | (17) (21) | 3 |

EXAMPLE 13

A photographic material having the following layer structure is produced:

| |
|---|
| Protective layer |
| Red-sensitive layer |
| Second gelatine intermediate layer |
| Green-sensitive layer |
| First gelatine intermediate layer |
| Blue-sensitive layer |
| Polyethylene base |

The gelatine layers comprise the following components (per m$^2$ of base material):

| Blue-sensitive layer | |
|---|---|
| Yellow coupler Y-2 | 859 mg |
| Tricresyl phosphate | 286 mg |
| Gelatine | 5.15 g |
| Curing agent | 300 mg |
| Wetting agent | 340 mg |
| AgBr | 520 mg |
| First gelatine intermediate layer | |
| Gelatine | 3.90 g |
| Curing agent | 230 mg |
| Wetting agent | 65 mg |
| Green-sensitive layer | |
| Magenta coupler M-5 | 306 mg |
| Tricresyl phosphate | 153 mg |
| Gelatine | 5.15 g |
| Curing agent | 300 mg |
| Wetting agent | 85 mg |
| AgBr | 260 mg |
| Stabiliser | 107 mg |
| Second gelatine intermediate layer | |
| Gelatine | 3.90 g |
| Curing agent | 230 mg |
| Wetting agent | 65 mg |
| Red-sensitive layer | |
| Cyan coupler E-6 | 331 mg |
| Tricresyl phosphate | 496 mg |
| Gelatine | 5.15 g |
| Curing agent | 300 mg |
| Wetting agent | 170 mg |
| AgBr | 260 mg |

A protective layer is produced with and without UV absorber

| | with UV absorber | without UV absorber |
|---|---|---|
| Gelatine | 1.2 g | 2.4 g |
| UV absorber | 300 mg | — |
| Tricresyl phosphate | 510 mg | — |
| Curing agent | 40 mg | 80 mg |
| Wetting agent | 100 mg | 200 mg |

| Sample No. | UV absorber |
|---|---|
| 85 | — |
| 86 | (3) |
| 87 | (4) |

The curing agent and wetting agent used are the corresponding compounds as in Example 1.

Three step wedges having a density difference of 0.15 kJ per step are exposed (with blue, green and red light) onto each of the 3 samples 75–77.

The samples are then processed by the EP2 process (Kodak) for colour negative paper.

After exposure and processing, the remission densities in red for the cyan step, in green for the magenta step and in blue for the yellow step are measured at a density of between 0.9 and 1.1 of the wedges. The wedges are then exposed in an Atlas exposure unit with a total of 15 kJ/cm$^2$, and the remission densities are remeasured.

The remission density before and after exposure is also measured for the magenta wedge in blue for yellowing.

The presence of the UV absorbers reduces the drop in dye density of the cyan, magenta and yellow image dye and the yellowing.

EXAMPLE 14

A photographic material having the following layer structure is produced:

| |
|---|
| Uppermost layer |
| Red-sensitive layer |
| Second gelatine intermediate layer |
| Green-sensitive layer |
| First gelatine intermediate layer |
| Blue-sensitive layer |
| Polyethylene base |

The gelatine layers comprise the following components (per m$^2$ of base material):
Blue-sensitive layer
α-(3-benzyl-4-ethoxyhydantoin-1-yl)-α-pivaloyl-2-chloro-5-[α-(2,4-di-t-amylphenoxy)-butanamido]acetanilide (400 mg) α-(1-butyl-phenylurazol-4-yl)-α-pivaloyl-5-(3-dodecansulfonyl-2-methylpropanamido)-2-methoxyacetamide (400 mg)
dibutylphthalate (130 mg)
dinonylphthalate (130 mg)
gelatine (1200 mg)
1,5-dioxa-3-ethyl-3-[β-(3,5-di-t-butyl-4-hydroxy-phenyl)propionyloxymethyl]-8,10-diphenyl-9-thia-[5,5]spiroundecane (150 mg)

bis(1-acryloyl-2,2,6,6-tetramethyl-4-piperidyl)2,2-bis-(3,5-di-t-butyl-4-hydroxybenzyl)malonate (150 mg)
3,5-di-t-butyl-4-hydroxy-(2,4-di-t-amylphenyl)-benzoate (150 mg)
Poly(N-t-butylacrylamide) (50 mg)
blue-sensitive silver chlorobromide emulsion (240 mg)
First gelatine intermediate layer
gelatine (1000 mg)
2,5-di-t-octylhydroquinone (100 mg)
5-[2,5-dihydroxy-4-(4-hexyloxycarbonyl-1,1-dimethylbutyl)phenyl]-5-methylhexanoic acid hexylester (100 mg)
dibutylphthalate (200 mg)
diisodecylphthalate (200 mg)
Green-sensitive layer
7-chloro-2-{2-[2-(2,4-di-t-amylphenoxy)octanamido]-1-methylethyl}-6-methyl-1H-pyrazolo[1,5-b][1,2,4]triazole (100 mg)
6-t-butyl-7-chloro-3-(3-dodecansulfonylpropyl)-1H-pyrazolo[5,1-o][1,2,4]triazole (100 mg)
dibutylphthalate (100 mg)
dikresylphosphate (100 mg)
trioctylphosphate (100 mg)
gelatine (1400 mg)
3,3,3',3'-tetramethyl-5,5',6,6'-tetrapropoxy-1,1'-spirobiindane (100 mg)
4-(i-tridecyloxyphenyl)thiomorpholine-1,1-dioxide (100 mg)
4,4'-butyliden-bis(3-methyl-6-t-butylphenol) (50 mg)
2,2'-isobutyliden-bis(4,6-dimethylphenol) (10 mg)
3,5-dichloro-4-(hexadecyloxycarbonyloxy)ethylbenzoate (20 mg)
3,5-bis[3-(2,4-di-t-amylphenoxy)propylcarbamoyl]sodium-benzolsulfinate (20 mg)
green-sensitive silver chlorobromide emulsion (150 mg)
Second gelatine intermediate layer
gelatine (1000 mg)
5-chloro-2-(3,5-di-t-butyl-2-hydroxyphenyl)benz-1,2,3-triazole (200 mg)
2-(3-dodecyl-2-hydroxy-5-methylphenyl)benz-1,2,3-triazole (200 mg)
trinonylphosphate (300 mg)
2,5-di-t-octylhydroquinone (50 mg)
5-[2,5-dihydroxy-4-(4-hexyloxycarbonyl-1,1-dimethylbutyl)phenyl]-5-methylhexanoic acid hexylester (50 mg)
Red-sensitive layer
2-[α-(2,4-di-t-amylphenoxy)butanamido]-4,6-di-chloro-5-ethylphenol (150 mg)
2,4-dichloro-3-ethyl-6-hexadecanamidophenol (150 mg)
4-chloro-2-(1,2,3,4,5-pentafluorobenzamido)-5-[2-(2,4-di-t-amylphenoxy)-3-methylbutanamido]phenol (100 mg)
dioctylphthalate (100 mg)
dicyclohexylphthalate (100 mg)
gelatine (1200 mg)
5-chloro-2-(3,5-di-t-butyl-2-hydroxyphenyl)benz-1,2,3-triazole (100 mg)
2-(3-dodecyl-2-hydroxy-5-methylphenyl)benz-1,2,3-triazole (100 mg)
3,5-di-t-butyl-4-hydroxy-(2,4-di-t-amylphenyl)-benzoate (50 mg)
Poly(N-t-butylacrylamide) (300 mg)
N,N-diethyl-2,4-di-t-amylphenoxyacetamide (100 mg)
2,5-di-t-octylhydroquinone (50 mg)
red-sensitive silver chlorobromide emulsion (200 mg)
The uppermost layer is produced with and without UV absorber with UV absorber:
2,5-di-t-octylhydroquinone (20 mg)
5-[2,5-dihydroxy-4-(4-hexyloxycarbonyl-1,1-dimethylbutyl)phenyl]-5-methylhexanoic acid hexylester (20 mg)
gelatine (400 mg)

trinonylphosphate (120 mg)
UV absorber Comp. No. (4) (200 mg)
without UV absorber:
gelatine (800 mg)

The curing agent used is 2,4-dichloro-6-hydroxytriazine, and the wetting agent used is the sodium salt of diisobutylnaphthalenesulfonic acid.

Three step wedges having a density difference of 0.15 kJ per step are exposed (with blue, green and red light) onto each of the 2 samples.

The samples are then processed by the RA-4 process (Kodak) for colour paper.

After exposure and processing, the remission densities in red for the cyan step, in green for the magenta step and in blue for the yellow step are measured at a density of between 0.9 and 1:1 of the wedges. The wedges are then exposed in an Atlas exposure unit with a total of 15 kJ/cm$^2$, and the remission densities are remeasured.

The remission density before and after exposure is also measured for the magenta wedge in blue for yellowing.

The presence of the UV absorbers reduces the drop in dye density of the cyan, magenta and yellow image dyes.

EXAMPLE 15

2,4,6-tris-[2-hydroxy-4-(3'(n-butoxy)- or 3'-(2-ethyl-hexyloxy)-2'-hydroxypropoxy)-phenyl]-1,3,5-triazine A mixture of 20.0 g (49.3 mmol) of 2,4,6-tris-(2,4-dihydroxy-phenyl)-1,3,5-triazine, 14.7 g (79.0 mmol) of 2-ethyl-hexyl-glycidyl ether, 10.3 g (79.0 mmol) of n-butyl-glycidyl ether, 1.8 g (4.9 mmol) of ethyl-triphenyl-phosphonium bromide in 100 ml of mesitylene is heated at 150° C. for 20 hours during which time the yellow suspension becomes a clear solution. The solvent is removed (rotavapor) and the crude product is dissolved in 50 ml of warm ethyl acetate and applied to a sintered buchner ($\phi=5$ cm) containing a layer of silicagel 60 (230–400 mesh). After elution with 1000 ml of ethyl acetate, the solvent is removed and drying at 120° C./0.01 mm; 3 hours, afforded 40.0 g (92% yield) of a mixture of 2,4,6-tris-[2-hydroxy-4-(3'-(n-butoxy)- or -3'-(2-ethyl-hexyloxy)-2'-hydroxy-propoxy)-phenyl-]1,3,5-triazine as tough thick pale yellow resin.

Analysis: $C_{48}H_{69}N_3O_{12}$: (880.09) Calc.: C 65.51; H 7.90; N 4.77%; Found: C 65.07; H 8.05; N 4.43%.

A sample of this material is recristallised in ethyl acetate to give a pale yellow solid, F. 75°–78° C. Thin layer chromatography (silicagel, $CH_2Cl_2$-methanol 95:5) indicates that all components in the initial mixture have cristallised out.

Analysis: $C_{48}H_{69}N_3O_{12}$: (880.09) Calc.: C 65.51; H 7.90; N 4.77%; Found: C 65.35; H 7.88; N 4.61%.

EXAMPLE 16

2,4,6-tris-[2-hydroxy-4-(3'-n-butoxy-2'-acetoxy-propoxy-phenyl]-1,3,5-triazine

To a suspension of 4.0 g (5.0 mmol) of 2,4,6-tris-[2-hydroxy-4-(3'-n-butoxy-2'-hydroxypropoxy)-phenyl]-1,3,5-triazine, 1.6 g (20 mmol) of acetyl chloride in 50 ml of toluene are added at 50° C., 3 drops of pyridine. The mixture is heated at 60° C. for 3 hours during which time hydrochloric acid is evolved. After removal of the solvent and excess of reagent (rotavapor), the crude product is dissolved in 300 ml of ethyl-acetate and filtered through a thin layer (1 cm) of silicagel 60 (230–400 mesh). Evaporation of the solvent affords 4.5 g (97% yield) of 2,4,6-tris-[2-hydroxy-4-(3'-n-butoxy-2'-acetoxy-propoxy)-phenyl]-1,3,5-triazine as a yellow semi-cristalline resin.

Analysis: $C_{48}H_{63}O_{15}N_3$: (922.04) Calc.: C 62.53; H 6.89; N 4.56%; Found: C 62.25; H 6.91; N 4.37%.

EXAMPLE 17

2,4,6-tris-[2-hydroxy-4(3'-n-butoxy-2'-valeroyloxy-propoxy)-phenyl]-1,3,5-triazine A mixture of 6.0 g (7.5 mmol) of 2,4,6-tris-[2-hydroxy-4-(3'-n-butoxy-2'-hydroxypropoxy)-phenyl]-1,3,5-triazine, 3.2 g (26.5 mmol) of valeroyl-chloride, 5 drops of pyridine in 50 ml of toluene is heated at 90° C. for 5 hours. Solvent is removed (rotavapor) and the crude product (9.3g) is subjected to a column chromatography [silicagel 60 (230–400 mesh); Eluant: petroleum ether-ethylacetate (4:1)]. The main fraction, after drying, gives 6.9 g (87.3% yield) of 2,4,6-tris-[2-hydroxy-4(3'-n-butoxy-2'-valeroyloxypropoxy)-phenyl]-1,3,5-triazine as a thick pale yellow resin.

Analysis: $C_{57}H_{81}O_{15}N_3$: (1048.21) Calc.: C 65.31; H 7.79; N 4.01%; Found: C 65.10; H 7.92; N 3.83%.

EXAMPLE 18

2,4,6-tris-[2-hydroxy-4-(3'(n-butoxy)- or -3'-(2-ethyl-hexyloxy)-2'-hydroxypropoxy)-phenyl]-1,3,5-triazine A mixture of 10.0 g (24.7 mmol) of 2,4,6-tris-(2,4-dihydroxy-phenyl)-1,3,5-triazine, 2.80 g (27.4 mmol) of ethyl-glycidyl ether, 3.50 g (26.8 mmol) of n-butyl-glycidyl ether, 5.10 g (27.3 mmol) of (2-ethyl-hexyl)-glycidyl ether and 0.9 g (2.4 mmol) of ethyltriphenyl-phosphonium bromide in 100 ml of mesitylene is heated at 140° C. under stirring for 24 hours, during which time the yellow suspension becomes a clear yellow solution. Solvent is removed (rotavapor) and the crude material is dissolved in 50 ml of warm ethyl acetate. This solution is applied onto a sintered glass Buchner ($\phi=8$ cm) containing a thin layer (3 cm) of silicagel 60 (230–400 mesh) and eluted with 1500 ml of ethyl acetate. After evaporation of the filtrate, the residue is dried at 130° C./0.1 mm; 3 hours to give 15.6 g (76.7% yield) of a mixture of 2,4,6-tris-[2-hydroxy-4-(3'(-n-butoxy)- or -3'-(ethoxy)-or -3'-(2-ethyl-hexyloxy)-2'-hydroxy-propoxy)-phenyl]1,3,5-triazine as a thick yellow resin.

Analysis: $C_{44}H_{61}N_3O_{12}$: (823.99) Calc.: C 64.14; H 7.46; N 5.10%; Found: C 64.07; H 7.64; N 4.96%.

EXAMPLE 19

2,4,6-tris-[2-hydroxy-4-(3'(-n-butoxy)- or -3'-(ethoxy)- or 3'-(isopropyloxy)-2'-hydroxy-propoxy)-phenyl]-1,3,5-triazines A mixture of 10.0 g (24.7 mmol) of 2,4,6-tris(2,4-dihydroxy-phenyl)-1,3,5-triazine, 2.80 g (27.4 mmol) of ethyl-glycidyl ether, 3.20 g (27.5 mmol) of glycidyl-isopropyl ether, 3.5 g (26.8 mmol) of n-butyl-glycidyl ether, 0.9 g (2.4 mmol) of ethyl-triphenyl-phosphonium bromide in 100 ml of mesitylene is heated at 140° C. under stirring for 24 hours. The starting yellow suspension becomes a clear yellow solution. Mesitylene is removed (rotavapor) and the crude material is dissolved in 50 ml of warm ethyl acetate. This solution is carried onto a sintered glass Buchner ($\phi=8$ cm) containing a thin layer (3 cm) of silicagel 60 (230–400 mesh). After elution with 1500 ml of ethyl acetate, the filtrate is evaporated and the residue is dried at 130° C./0.1 mm; 3 hours. There are obtained 15.5 g (83.5 % yield) of a mixture of 2,4,6-tris-[2-hydroxy-4-(3'(-n-butoxy)- or -3'-(ethoxy)- or -3'-(isopropyloxy)-2'-hydroxy-propoxy)-phenyl]-1,3,5-triazines as a thick dark yellow resin.

Analysis: $C_{39}H_{51}N_3O_{12}$ (753.85) Calc.: C 62.14; H 6.82; N 5.57%; Found: C 62.14; H 7.03; N 5.32%.

EXAMPLE 20

2,4,6-tris-[2-hydroxy-4-(3'-allyloxy- or -3'-n-butyloxy-2'-hydroxy-propoxy)phenyl]-1,3,5-triazine A mixture of 10.0 g (24.7 mmol) of 2,4,6-tris-(2,4-dihydroxy-phenyl)-1,3,5-triazine, 5.14 g (39.5 mmol) of n-butyl-glycidyl-ether, 4.51 g (39.5 mmol) of allyl-glycidyl-ether, 0.9 g (2.4 mmol) of ethyl-triphenyl-phosphonium bromide in 100 ml of mesitylene is heated under stirring at 140° C. for 24 hours. The initial suspension becomes a clear yellow solution. The solvent is removed (rotavapor) and the crude material is dissolved in 50 ml of warm ethyl acetate. This solution is applied onto a sintered buchner ($\phi=8$ cm) containing a thin layer (3 cm) of silicagel 60 (230–400 mesh). After elution with 1500 ml of ethyl acetate, the filtrate is evaporated and the residue is dried at 130° C./0.1 mm; 3 hours. There are obtained 12.6 g (66.2% yield) of a mixture of 2,4,6-tris-[2-hydroxy-4-(3'-allyloxy- or -3'-n-butyloxy-2'-hydroxy-propoxy)-phenyl]-1,3,5-triazine as a thick yellow resin.

Analysis: $C_{40.5}H_{51}N_3O_{12}$; (771.87) Calc.: C 63.02; H 6.66; N 5.44%; Found: C 62.84; H 6.73; N 5.38%.

EXAMPLE 21

2,4,6-tris-[2-hydroxy-4-(3'-(ethyloxy)- or -3'-(2-ethyl-hexyloxy)-2'-hydroxypropoxy)-phenyl]-1,3,5-triazine A mixture of 10.0 g (23.7 mmol) of 2,4,6-tris-(2,4-dihydroxy-phenyl)-1,3,5-triazine, 7.40 g (39.7 mmol) of (2-ethyl-hexyl)-glycidyl ether, 4.0 g (39.5 mmol) of ethyl-glycidyl ether, 0.9 g (2.4 mmol) of ethyl-triphenylphosphonium bromide in 100 ml of mesitylene is heated at 140° C. under stirring for 24 hours. The initial yellow suspension becomes a clear yellow solution. Mesitylene is removed (rotavapor). The crude material, dissolved in 50 ml of ethyl acetate is applied onto a sintered glass Buchner ($\phi=8$ cm) containing a thin layer (2 cm) of silicagel 60 (230–400 mesh). After elution with 1000 ml of ethyl acetate, the filtrate is evaporated and the residue is dried at 130° C./0.1 mm; 3 hours. There are obtained 16.2 g (78.4% yield) of a mixture of 2,4,6-tris-[2-hydroxy-4-(3'-(ethyloxy)or -3'-(2-ethyl-hexyloxy)-2'-hydroxy-propoxy)-phenyl]-1,3,5-triazine as a thick yellow resin.

Analysis: $C_{45}H_{63}N_3O_{12}$ (838.02) Calc.: C 64.50; H 7.58; N 5.01%; Found: C 64.75; H 7.81; N 4.76%.

EXAMPLE 22

2,4,6-tris-[2-hydroxy-4-(3'-(tert-butoxy)- or -3'-(2-ethyl-hexyloxy)-2'-hydroxy-propoxy)-phenyl]-1,3,5-triazine A mixture of 10.0 g (24.7 mmol) of 2,4,6-tris-(2,4-dihydroxy-phenyl)-1,3,5-triazine, 7.35 g (39.5 mmol) of (2-ethyl-hexyl)-glycidyl ether, 5.14 g (39.5 mmol) of tert.-butylglycidyl ether, 0.9 g (2.4 mmol) of ethyl-triphenyl-phosphonium bromide in 100 ml of mesitylene is heated at 140° C. under stirring for 24 hours during which time the yellow suspension becomes a yellow clear solution. The solvent is evaporated (rotavapor). The crude product is dissolved in 50 ml of warm ethyl acetate and applied to a sintered glass Buchner ($\phi = 8$ cm) containing a thin layer (h=3 cm) of silicagel 60(230–400 mesh). The product is eluted by 1000 ml of ethyl acetate. Removal of the solvent and drying of the residue at 130° C./0.1 mm; 3 hours gives 17.6 g (81.0% yield) of a mixture of 2,4,6-tris-[2-hydroxy-4-(3'-(tert.-butoxy)-or -3'-(2-ethyl-hexyloxy)-2'-hydroxy-propoxy)-phenyl]-1,3,5-triazine as a thick brown resin.

Analysis: $C_{48}H_{69}N_3O_{12}$(880.09) Calc.: C 65.51; H 7.90; N 4.77%; Found: C 65.25; H 8.07; N 4.58%.

EXAMPLE 23

2,4,6-tris-[2-hydroxy-4-(3'(-n-butoxy)- or -3'-(tert.-butoxy)- or -3'-(2-ethyl-hexyloxy)-2'-hydroxy-propoxy)-phenyl]-1,3,5-triazine A mixture of 10.0 g (24.7 mmol) of 2,4,6-tris-(2,4-dihydroxy-phenyl)-1,3,5-triazine, 3.53 g (27.1 mmol) of n-butyl-glycidyl ether, 3.53 g (27.1 mmol) of tert.-butyl-glycidyl ether, 5.10 g (27.3 mmol) of (2-ethyl-hexyl)-glycidyl ether and 0.9 g (2.4 mmol) of ethyltriphenyl-phosphonium bromide in 100 ml of mesitylene is heated at 140° C. under stirring for 24 hours. The starting yellow suspension becomes a brown clear solution. Mesitylene is removed (rotavapor) and the crude material is dissolved in 50 ml of warm ethyl acetate. This solution is carried onto a sintered glass Buchner ($\phi = 8$ cm) containing a thin layer (3 cm) of silicagel 60 (230–400 mesh). After elution with 1500 ml of ethyl acetate, the filtrate is evaporated and the residue is dried at 130° C./0.1 mm; 3 hours. There are obtained 17.6 g (83.7% yield) of a mixture of 2,4,6-tris-[2-hydroxy-4-(3'(-n-butoxy)- or -3'-(tert.-butoxy)- or -3'-(2-ethyl-hexyloxy)-2'-hydroxy-propoxy)-phenyl]-1,3,5-triazine as a thick yellow resin.

Analysis: $C_{46}H_{65}N_3O_{12}$(852.04) Calc.: C 64.85; H 7.69; N 4.93%; Found: C 64.94; H 7.80; N 4.84%.

EXAMPLE 24

To a solution of 15.0 g of 2,4,6-tris-[2-hydroxy-4-(2'-hydroxy-3'-butoxypropyloxy)phenyl]-1,3,5-triazine and 8.47 g of imidazole in 112 ml of N,N'-dimethylacetamide are added dropwise 11.12 g of thexyl-dimethyl-chloro silane under a nitrogen atmosphere. After 20 hours at room temperature the reaction mixture is evaporated (rotavapor). The residue is filtered through a layer of silicagel (eluant:hexane/ethyl-acetate 30:1). 14.1 g of the compound of the formula

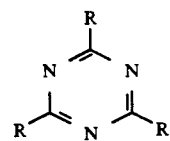

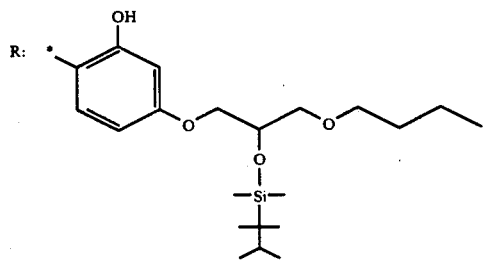

are obtained as a yellow resin.

Analysis: $C_{66}H_{111}N_3O_{12}Si_3$: Calc.: C 64.82; H 9.15; N 3.44%; Found: C 65.00; H 9.38; N 3.05%.

What is claimed is:

1. A photographic material comprising, on a base, blue-sensitive, green-sensitive and/or red-sensitive silver-halide emulsion layers and, if desired, a protection layer, a layer containing a UV absorber being arranged between the uppermost silver-halide emulsion layer and the protection layer, or on top of the uppermost silver-halide layer, wherein the UV absorber conforms to the formula

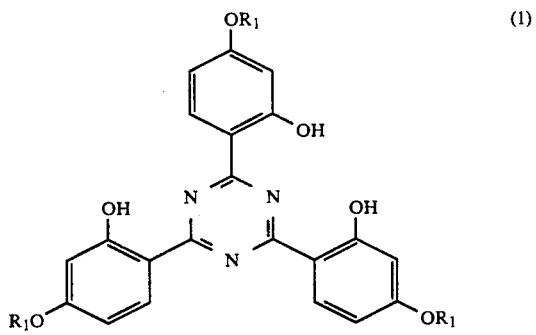

(1)

in which the radicals $E_1$, $E_2$ and $E_3$, independently of one another, are alkyl having 1 to 18 carbon atoms substituted by $—CO_2R_2$, where $R_2$ is alkyl having 1 to 18 carbon atoms, or oxygen-, sulfur- or nitrogen-interrupted alkyl or hydroxyalkyl having 3 to 30 carbon atoms, hydroxyalkyl having 2 to 18 carbon atoms, alkenyl having 3 to 18 carbon atoms, glycidyl, cycloalkyl having 5 to 8 carbon atoms, benzyl, alkylphenyl having 1 to 12 carbon atoms in the alkyl moiety, phenyl, furfuryl or a radical of the formula $—CH_2CH(OH)R_7$, $R_7$ is phenylalkyl having 1 to 6 carbon atoms in the alkyl moiety or a radical of the formula $—CH_2OR_8$, and $R_8$ is cyclohexyl, benzyl, phenyl or tolyl; or the radicals $E_1$, $E_2$ and $E_3$, independently of one another, are radicals of the formula $—CH_2—CH(OR_x)R_y$, $—CH_2CH(OR_x)CH_2OR_z$,

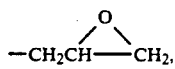

—CH$_2$COR$_y$ or —CH$_2$COCH$_2$OR$_z$, where
R$_x$ is H, —COR$_s$, —COOR$_w$ or —SiR$_p$R$_q$R$_r$,
R$_y$ is C$_1$-C$_{18}$alkyl or phenyl-C$_1$-C$_4$alkyl,
R$_z$ is C$_1$-C$_{18}$alkyl, C$_2$-C$_{18}$alkenyl, phenyl-C$_1$-C$_4$alkyl, —COR$_s$ or oxygen-interrupted C$_2$-C$_{24}$alkyl or C$_2$-C$_{24}$hydroxyalkyl,
R$_s$ is C$_1$-C$_{18}$alkyl, C$_2$-C$_{18}$alkenyl or phenyl,
R$_w$ is C$_1$-C$_4$alkyl, and
R$_p$, R$_q$ and R$_r$, independently of one another, are C$_1$-C$_6$alkyl or phenyl; or
the radicals E$_1$, E$_2$ and E$_3$, independently of one another, are G-II groups, where II is a group of the formula

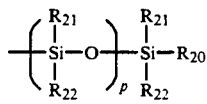

and G is a direct bond or a divalent group of one of the following formulae:

—(CH$_2$)$_q$—, —(CH$_2$)$_q$—O—, —(CH$_2$)$_q$—O—R$_{26}$—,

—(CH$_2$)$_q$—CO—X—(CH$_2$)$_r$—,

—(CH$_2$)$_q$—CO—X—(CH$_2$)$_r$—O—,

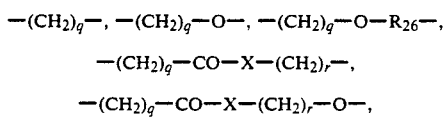

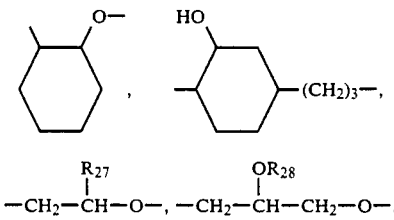

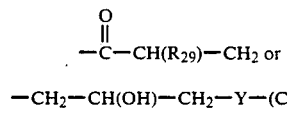

—CH$_2$—CH(OH)—CH$_2$—Y—(CH$_2$)$_q$—, in which q and r, independently of one another, are 1-4 and p is 0-50.
R$_{26}$ is C$_1$-C$_{12}$alkylene, cyclohexylene or phenylene,
R$_{27}$ is C$_1$-C$_{12}$alkyl, C$_5$-C$_8$cycloalkyl, phenyl, C$_2$-C$_{13}$alkoxymethyl, C$_6$-C$_9$cycloalkoxymethyl or phenoxymethyl,
R$_{28}$ is a group of the formula G-II,
R$_{29}$ is hydrogen or methyl,
X is —O— or —NR$_{23}$—, in which R$_{23}$ is hydrogen, C$_1$-C$_{12}$alkyl or a —(CH$_2$)$_3$—G-II or —(CH$_2$)$_3$—O—G-II group,
Y is —O— or —NH—, and
R$_{20}$, R$_{21}$ and R$_{22}$, independently of one another, are C$_1$-C$_{18}$alkyl, cyclohexyl, phenyl or C$_1$-C$_{18}$alkoxy.

2. A photographic material according to claim 1, wherein the radicals E$_1$, E$_2$ and E$_3$, independently of one another, are radicals of the formula —CH$_2$—CH(OR$_x$)R$_y$, —CH$_2$CH(OR$_x$)CH$_2$OR$_z$, —CH$_2$COR$_y$ or —CH$_2$COCH$_2$OR$_z$, where R$_x$ is H, —COR$_s$, —COOR$_w$ or —SiR$_p$R$_q$R$_r$, R$_y$ is C$_1$-C$_8$alkyl, R$_z$ is C$_1$-C$_{18}$alkyl, C$_2$-C$_{18}$alkenyl, benzyl, —COR$_s$ or oxygen-interrupted C$_2$-C$_{24}$alkyl or C$_2$-C$_{24}$hydroxyalkyl, R$_s$ is C$_1$-C$_{18}$alkyl, C$_2$-C$_{18}$alkenyl or phenyl, R$_w$ is C$_1$-C$_4$alkyl, and R$_p$, R$_q$ and R$_r$, independently of one another, are C$_1$-C$_6$alkyl; or E$_1$, E$_2$ and E$_3$ are a G-II group, where II is a group of the formula

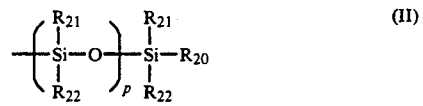

and G is a direct bond or a divalent group of one of the following formulae: —(CH$_2$)$_q$—, —(CH$_2$)$_q$—O—, —(CH$_2$)$_q$—CO—X—(CH$_2$)$_r$—,

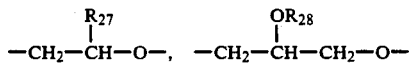

or —CH$_2$—CH(OH)—CH$_2$—Y—(CH$_2$)$_q$—, in which q and r, independently of one another, are 1, 2 or 3 and p is 0-50, R$_{27}$ is methyl, phenyl, C$_3$-C$_9$alkoxymethyl or phenoxymethyl, R$_{28}$ is a group of the formula G-II, X and Y are —O—, R$_{20}$, R$_{21}$ and R$_{22}$, independently of one another, are C$_1$-C$_8$alkyl, phenyl or C$_1$-C$_8$alkoxy.

3. A photographic material comprising, on a base, blue-sensitive, green-sensitive and/or red-sensitive silver-halide emulsion layers and a protection layer, a layer containing a UV absorber being arranged between the uppermost silver-halide emulsion layer and the protection layer, wherein (a) the UV absorber conforms to the formula

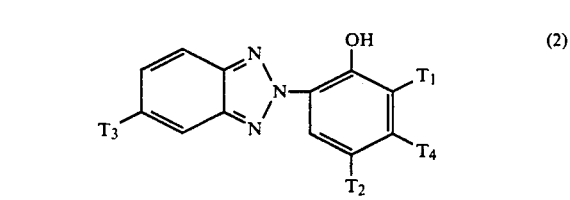

in which T$_1$, T$_2$ and T$_3$, independently of one another, are hydrogen, halogen, alkyl, carboxylate-substituted alkyl, alkoxy, aryloxy, hydroxyl or acyloxy, and T$_4$ is hydrogen, alkoxy, aryloxy or acyloxy, and (b) the material contains at least one further layer containing a UV absorber of the formula (1) as defined in claim 1.

4. A photographic material comprising, on a base, at least two silver-halide emulsion layers with a UV absorber-containing layer between these layers, wherein the UV absorber conforms to the formula (1) as defined in claim 1.

5. A photographic material comprising, on a base, a red-sensitive silver-halide emulsion layer and, if desired, blue-sensitive and/or green-sensitive silver-halide emulsion layers, wherein the red-sensitive silver-halide emulsion layer contains a UV absorber of the formula (1) as defined in claim 1.

6. A photographic material according to claim 1, wherein a mixture of the UV absorbers of the formulae (1) and (2) is present in the layers which may contain a UV absorber.

7. A photographic material according to claim 3, wherein a mixture of the UV absorbers of the formulae (1) and (2) is present in the layers which may contain a UV absorber.

8. A photographic material according to claim 4, wherein a mixture of the UV absorbers of the formulae (1) and (2) is present in the layers which may contain a UV absorber.

9. A photographic material according to claim 5, wherein a mixture of the UV absorbers of the formulae (1) and (2) is present in the layers which may contain a UV absorber.

10. A photographic material according to claim 1, wherein the red-sensitive silver-halide emulsion layer contains a cyan coupler of the formula

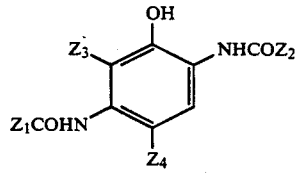
(E-7)

and/or of the formula

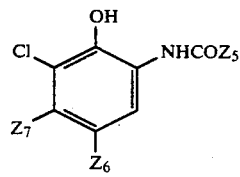
(E-8)

in which $Z_1$ is alkyl or aryl, $Z_2$ is alkyl, cycloalkyl, aryl, heterocyclic group or a ballast group, $Z_3$ is hydrogen or halogen, $Z_1$ and $Z_3$ together can form a ring, and $Z_4$ is hydrogen or a leaving group, and $Z_5$ is a ballast group, $Z_6$ is hydrogen or a leaving group, and $Z_7$ is alkyl.

11. A photographic material according to claim 3, wherein the red-sensitive silver-halide emulsion layer contains a cyan coupler of the formula

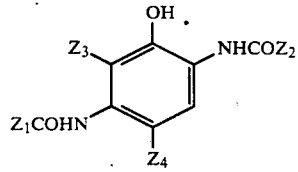
(E-7)

and/or of the formula

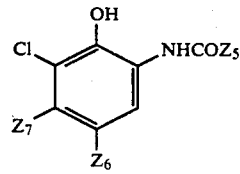
(E-8)

in which $Z_1$ is alkyl or aryl, $Z_2$ is alkyl, cycloalkyl, aryl, a heterocyclic group or a ballast group, $Z_3$ is hydrogen or halogen, $Z_1$ and $Z_3$ together can form a ring, and $Z_4$ is hydrogen or a leaving group, and $Z_5$ is a ballast group, $Z_6$ is hydrogen or a leaving group, and $Z_7$ is alkyl.

12. A photographic material according to claim 4, wherein the red-sensitive silver-halide emulsion layer contains a cyan coupler of the formula

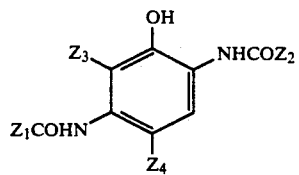
(E-7)

and/or of the formula

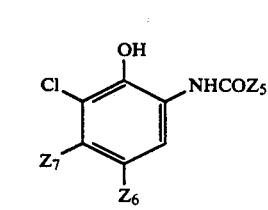
(E-8)

in which $Z_1$ is alkyl or aryl, $Z_2$ is alkyl, cycloalkyl, aryl, a heterocyclic group or a ballast group, $Z_3$ is hydrogen or halogen, $Z_1$ and $Z_3$ together can form a ring, and $Z_4$ is hydrogen or a leaving group, and $Z_5$ is a ballast group, $Z_6$ is hydrogen or a leaving group, and $Z_7$ is alkyl.

13. A photographic material according to claim 5, wherein the red-sensitive silver-halide emulsion layer contains a cyan coupler of the formula

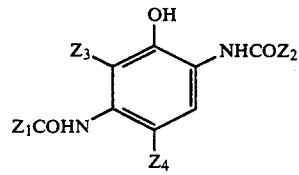
(E-7)

and/or of the formula

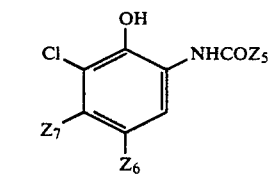
(E-8)

in which $Z_1$ is alkyl or aryl, $Z_2$ is alkyl, cycloalkyl, aryl, a heterocyclic group or a ballast group, $Z_3$ is hydrogen or halogen, $Z_1$ and $Z_3$ together can form a ring, and $Z_4$ is hydrogen or a leaving group, and $Z_5$ is a ballast group, $Z_6$ is hydrogen or a leaving group, and $Z_7$ is alkyl.

14. A photographic material according to claim 1, wherein the green-sensitive silver-halide emulsion layer contains a magenta coupler of the formula

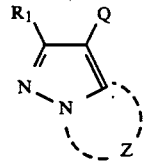
(M-7)

in which $R_1$ is hydrogen or a substituent, Z represents the non-metallic atoms necessary for completion of a 5-membered ring containing 2 or 3 nitrogen atoms, it being possible for this ring to be substituted, and Q is hydrogen or a leaving group.

15. A photographic material according to claim 3, wherein the green-sensitive silver-halide emulsion layer contains a magenta coupler of the formula

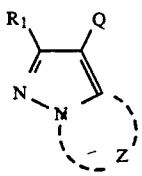

(M-7)

in which $R_1$ is hydrogen or a substituent, Z represents the non-metallic atoms necessary for completion of a 5-membered ring containing 2 or 3 nitrogen atoms, it being possible for this ring to be substituted, and Q is hydrogen or a leaving group.

16. A photographic material according to claim 4, wherein the green-sensitive silver-halide emulsion layer contains a magenta coupler of the formula

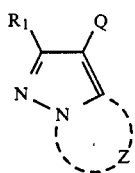

(M-7)

in which $R_1$ is hydrogen or a substituent, Z represents the non-metallic atoms necessary for completion of a 5-membered ring containing 2 or 3 nitrogen atoms, it being possible for this ring to be substituted, and Q is hydrogen or a leaving group.

17. A photographic material according to claim 5, wherein the green-sensitive silver-halide emulsion layer contains a magenta coupler of the formula

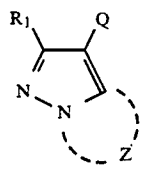

(M-7)

in which $R_1$ is hydrogen or a substituent, Z represents the non-metallic atoms necessary for completion of a 5-membered ring containing 2 or 3 nitrogen atoms, it being possible for this ring to be substituted, and Q is hydrogen or a leaving group.

18. A photographic material according to claim 1, wherein the green-sensitive silver-halide emulsion layer contains a magenta coupler of the formula

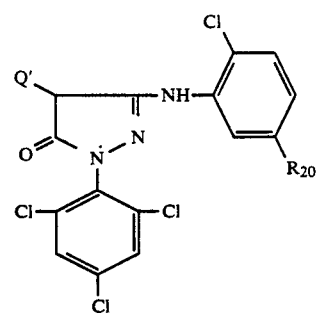

in which $R_{20}$ is hydrogen, alkyl, acylamino, carbamoyl, sulfamoyl, sulfonamido, alkoxycarbonyl, acyloxy or a urethane group, and $Q'$ is a leaving group.

19. A photographic material according to claim 3, wherein the green-sensitive silver-halide emulsion layer contains a magenta coupler of the formula

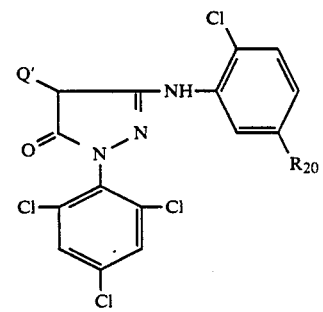

in which $R_{20}$ is hydrogen, alkyl, acylamino, carbamoyl, sulfamoyl, sulfonamido, alkoxycarbonyl, acyloxy or a urethane group, and $Q'$ is a leaving group.

20. A photographic material according to claim 4, wherein the green-sensitive silver-halide emulsion layer contains a magenta coupler of the formula

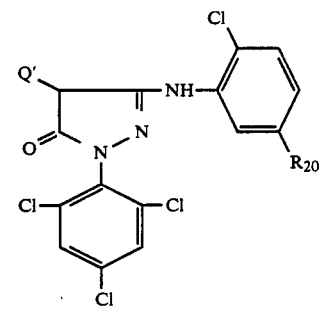

in which $R_{20}$ is hydrogen, alkyl, acylamino, carbamoyl, sulfamoyl, sulfonamido, alkoxycarbonyl, acyloxy or a urethane group, and $Q'$ is a leaving group.

21. A photographic material according to claim 5, wherein the green-sensitive silver-halide emulsion layer contains a magenta coupler of the formula

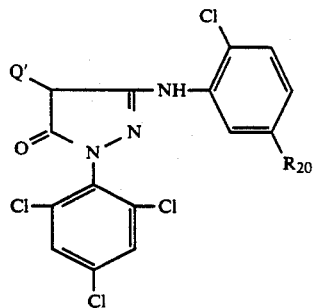

in which $R_{20}$ is hydrogen, alkyl, acylamino, carbamoyl, sulfamoyl, sulfonamido, alkoxycarbonyl, acyloxy or a urethane group, and Q' is a leaving group.

22. A photographic material according to claim 1 containing a further layer between the green-sensitive and red-sensitive silver halide emulsion layers, wherein a UV absorber of either formula (1) as defined in claim 25 or of the formula (2)

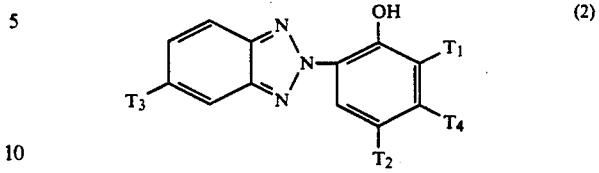

in which $T_1$, $T_2$ and $T_3$, independently of one another, are hydrogen, halogen, alkyl, carboxylate-substituted alkyl, alkoxy, aryloxy, hydroxyl or acyloxy, and $T_4$ is hydrogen, alkoxy, aryloxy or acyloxy, is present in the further layer and a UV absorber of either formula (1) or of formula (2) is present in the red-sensitive silver halide emulsion layer.

* * * * *